Figure 1C:
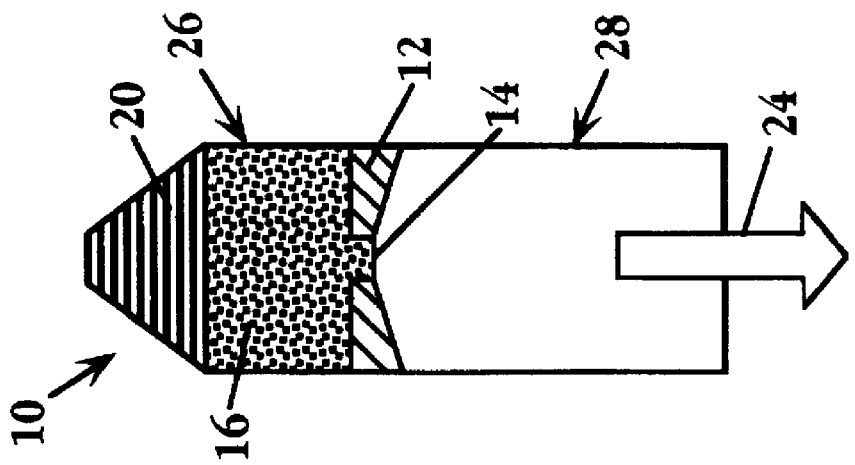

United States Patent [19]
Van Vlasselaer

[11] Patent Number: 5,840,502
[45] Date of Patent: *Nov. 24, 1998

[54] METHODS FOR ENRICHING SPECIFIC CELL-TYPES BY DENSITY GRADIENT CENTRIFUGATION

[75] Inventor: Peter Van Vlasselaer, Sunnyvale, Calif.

[73] Assignee: Activated Cell Therapy, Inc., Mountain View, Calif.

[*] Notice: The term of this patent shall not extend beyond the expiration date of Pat. No. 5,474,687.

[21] Appl. No.: 299,467

[22] Filed: Aug. 31, 1994

[51] Int. Cl.$^6$ .......................... G01N 33/567; B01L 11/00
[52] U.S. Cl. .................. 435/7.21; 210/781; 210/782; 435/2; 435/7.23; 435/7.24; 435/803; 436/514; 436/518; 436/527; 436/824; 422/72; 422/101; 422/102
[58] Field of Search ..................................... 210/781, 782; 435/2, 7.21, 7.23, 7.24, 803; 436/514, 518, 527, 824; 422/72, 101, 102

[56] References Cited

U.S. PATENT DOCUMENTS

| | | | |
|---|---|---|---|
| 3,441,205 | 4/1969 | Young, Jr. . | |
| 3,513,976 | 5/1970 | James . | |
| 3,706,305 | 12/1972 | Berger et al. | 128/762 |
| 3,706,306 | 12/1972 | Berger et al. | 128/762 |
| 3,750,645 | 8/1973 | Bennett et al. | 128/760 |
| 3,849,072 | 11/1974 | Ayres | 210/789 |
| 3,862,303 | 1/1975 | Anderson | 436/531 |
| 3,937,211 | 2/1976 | Merten | 128/765 |
| 3,957,654 | 5/1976 | Ayres | 210/516 |
| 3,957,741 | 5/1976 | Rembaum et al. | 526/312 |
| 3,965,889 | 6/1976 | Sachs | 128/764 |

(List continued on next page.)

FOREIGN PATENT DOCUMENTS

| | | |
|---|---|---|
| 0595641A2 | 10/1993 | European Pat. Off. . |
| WO 91/07660 | 5/1991 | WIPO . |
| WO 93/08268 | 4/1993 | WIPO . |
| WO 93/08269 | 4/1993 | WIPO . |

OTHER PUBLICATIONS

Blanchard et al., "Infiltration of Interleukin–2–inducible Killer Cells in Ascitic Fluid and Pleural Effusions of Advanced Cancer Patients," *Cancer Research*, vol. 48, pp. 6321–6327, (1988).

Wallach et al., "Affinity Density Perturbation: A New Fractionation Principle and Its Illustration in a Membrane Separation," *FEBS Letters*, vol. 21, No. 1, pp. 29–33, (1972).

"The CD System," Dako, Inc., (1990).

Dicke et al., 1968, "The Selective Elimination of Immunologically Competent Cells From Bone Marrow and Lymphatic Cell Mixtures," *Transplantation* 6(4):562–570.

Dicke et al., 1970, "Avoidance of Acute Secondary Disease by Purification of Hemopoietic Stem Cells with Density Gradient Centrifugation," *Exp. Hematol.* 20:126–130.

(List continued on next page.)

*Primary Examiner*—Lora M. Green
*Assistant Examiner*—Susan C. Wolski
*Attorney, Agent, or Firm*—Carol A. Stratford; Debra J. Glaister; Peter J. Dehlinger

[57] ABSTRACT

The present invention relates to methods of enriching for desired cell population from cell sources, such as body fluids, dispersed tissue specimens and cultured cells. In particular, the present invention relates to the use of a cell-trap centrifugation tube containing a specific density gradient solution adjusted to the specific density of a desired cell population to enrich for the desired cell from a cell source. The tube allows the desired cell population to be collected by decantation after centrifugation to minimize cell loss and maximize efficiency. In addition, the method can be further simplified by density-adjusted cell sorting which uses cell type-specific binding agents such as antibodies and lectins linked to carrier particles to impart a different density to the undesired populations in a more convenient manner. The rapid cell enrichment method described herein has a wide range of diagnostic and therapeutic applications.

13 Claims, 16 Drawing Sheets

U.S. PATENT DOCUMENTS

| | | | |
|---|---|---|---|
| 3,985,122 | 10/1976 | Topham | 128/765 |
| 4,001,122 | 1/1977 | Griffin | 210/516 |
| 4,020,831 | 5/1977 | Adler | 128/765 |
| 4,022,576 | 5/1977 | Parker | 436/177 |
| 4,035,316 | 7/1977 | Yen et al. | 521/65 |
| 4,040,959 | 8/1977 | Berman et al. | 210/782 |
| 4,055,501 | 10/1977 | Cornell | 210/516 |
| 4,066,414 | 1/1978 | Selby | 422/102 |
| 4,105,598 | 8/1978 | Yen et al. | 521/53 |
| 4,112,924 | 9/1978 | Ferrara et al. | 128/764 |
| 4,134,512 | 1/1979 | Nugent | 215/247 |
| 4,147,628 | 4/1979 | Bennett et al. | 210/789 |
| 4,152,270 | 5/1979 | Cornell | 210/516 |
| 4,181,700 | 1/1980 | Chervenka et al | 422/102 |
| 4,213,456 | 7/1980 | Böttger | 604/226 |
| 4,256,120 | 3/1981 | Finley | 128/764 |
| 4,378,812 | 4/1983 | Sarstedt | 128/765 |
| 4,443,345 | 4/1984 | Wells | 210/782 |
| 4,459,997 | 7/1984 | Sarstedt | 128/764 |
| 4,510,244 | 4/1985 | Parks et al. | 435/172.2 |
| 4,511,349 | 4/1985 | Nielsen et al. | 494/16 |
| 4,511,662 | 4/1985 | Baran et al. | 436/513 |
| 4,533,468 | 8/1985 | Ensor et al. | 209/172 |
| 4,562,844 | 1/1986 | Carpenter et al. | 128/675 |
| 4,569,764 | 2/1986 | Satchell | 210/511 |
| 4,610,846 | 9/1986 | Martin | 422/101 |
| 4,707,276 | 11/1987 | Dodge et al. | 210/789 |
| 4,710,472 | 12/1987 | Saur et al. | 435/308.1 |
| 4,777,145 | 10/1988 | Luotola et al. | 436/526 |
| 4,824,560 | 4/1989 | Alspector | 209/208 |
| 4,828,716 | 5/1989 | McEwen et al. | 210/740 |
| 4,844,818 | 7/1989 | Smith | 210/789 |
| 4,886,071 | 12/1989 | Mehl et al. | 128/760 |
| 4,917,801 | 4/1990 | Luderer et al. | 210/516 |
| 4,927,749 | 5/1990 | Dorn | 435/2 |
| 4,927,750 | 5/1990 | Dorn | 435/2 |
| 4,954,264 | 9/1990 | Smith | 210/782 |
| 4,957,638 | 9/1990 | Smith | 210/782 |
| 4,983,369 | 1/1991 | Barder et al. | 423/338 |
| 5,030,341 | 7/1991 | McEwen et al. | 210/94 |
| 5,030,559 | 7/1991 | Nicolson et al. | 435/7.23 |
| 5,039,401 | 8/1991 | Columbus et al. | 210/177 |
| 5,045,201 | 9/1991 | Dubois et al. | 210/502.1 |
| 5,053,134 | 10/1991 | Luderer et al. | 210/516 |
| 5,132,232 | 7/1992 | Parker | 436/177 |
| 5,236,604 | 8/1993 | Fiehler | 210/782 |
| 5,248,480 | 9/1993 | Greenfield et al. | 422/68.1 |
| 5,260,186 | 11/1993 | Cercek et al. | 435/2 |
| 5,269,927 | 12/1993 | Fiehler | 210/516 |
| 5,271,852 | 12/1993 | Luoma, II | 210/789 |
| 5,279,936 | 1/1994 | Vorpahl | 435/6 |
| 5,308,506 | 5/1994 | McEwen | 210/745 |
| 5,474,687 | 12/1995 | Van Vlasselaer | 210/782 |

OTHER PUBLICATIONS

Dicke et al., 1971, "Allogeneic Bone Marrow Transplantation After Elimination of Immunocompetent Cells by Means of Density Gradient Centrifugation," *Transplantation Proceedings* 3(1):666–668.

Dicke et al., 1973, "The Use of Stem Cell Concentrates As Bone Marrow Grafts in Man," *Transplantation Proceedings* 5(1):909–912.

Korbling et al., 1977, "Procurement of Human Blood Stem Cells by Continuous–Flow Centrifugation—Further Comment," *Blood* 50:753–754.

Korbling et al., 1977, "In–Vitro and In–Vivo Properties of Canine Blood Mononuclear Leukocytes Separated by Discontinuous Albumin Density Gradient Centrifugation," *Biomedicine* 26:275–283.

Herzenberg et al., 1979, "Fetal Cells in the Blood of Pregnant Women: Detection and Enrichment by Fluorescence–Activated Cell Sorting" *Proc. Natl. Aca. Sci. USA* 76:1453–5.

Olofsson et al., 1980, "Separation of Human Bone Marrow Cells in Density Gradients of Polyvinylpyrrolidone Coated Silica Gel (Percoll)," *Second J. Heematol.* 24:254–262.

Osborne et al., 1980, "The Value of Estrogen and Progesterone Receptorsin the Treatment of Breast Cancer", *Cancer* 46(12):2884–8.

Westley et al., 1980, "An Estrogen–Induced Protein Secreted By Human–Breast Cancer–Cells in Culture" *European Journal of Cell Biology* 22(1):397.

Gerdes et al., 1983, "Production of a Mouse Monoclonal Antibody Reactive with a Human Nuclear" *Current Biotech Abs.*

Ellis et al., 1984, "The Use of Discontinuous Percoll Gradients to Separate Populations of Cells from Human Bone Marrow and Peripheral Blood," *J. of Immunological Methods* 66:9–16.

Kufe et al., 1984, "Differential Reactivity of a Novel Monoclonal Antibody (DF3) with Human Malignant Versus Benign Breast Tumors" *Hybridoma* 3(3):223–32.

Lasky et al., 1985, "Size and Density Characterization of Human Committed and Multipotent Hematopoietic Progenitors" *Exp. Hematol.* 13:680–4.

Martin et al., 1986, "Purification of Haemopoietic Progenitor Cells From Patients with Chronic Granulocytic Leukaemia Using Percoll Density Gradients and Elutriation" *Brit. J. Haematol.* 63:187–98.

Bray et al., 1987 "Serum Levels and Biochemical Characteristics of Cancer–Associated Antigen CA–549, a Circulating Breast Cancer Marker" *Cancer Res* 47(22):5853–60.

Bianchi et al., 1990, "Isolation of fetal DNA from nucleated erythrocytes in maternal blood," *Proc. Natl. Acad. Sci. USA* 87:3279–3283.

Price et al., 1991, "Prenatal diagnosis with fetal cells isolated from maternal blood by multiparameter flow cytometry," *Am. J. Obstet. Gynecol.* 165(6, part 1):1731–1737.

Shpall et al., 1991, "Immunomagnetic purging of breast cancer from bone marrow for autologous transplantation," *Bone Marrow Transplantation* 7:145–151.

Yoshioka et al., 1991, "Immobilization of ultra–thin layer of monoclonal antibody on glass surface," *J. of Chromolography* 566:361–368.

Durrant et al., 1992 "A Rapid Method for Separating Tumour Infiltrating Cells and Tumour Cells from Colorectal Tumours" *J. Immunol. Meth.* 147:57–64.

Elias et al., 1992, Session 12: Plenary Session, "Prenatal diagnosis of aneuploidy using fetal cells isolated from maternal blood" *Am. J. Hum. Genet.* 51:A4, Excerpt 5.

Ganshirt–Ahlert et al., 1992, Session 34: Prenatal and Perinatal Genetics II, and Molecular Applications in Clinical Genetics III, "Noninvasive prenatal diagnosis," *Am. J. Hum. Genet.* 51:A48 Excerpt 182.

Ganshirt–Ahlert et al., 1992, "Magnetic cell sorting and the transferrin receptor as potential means of prenatal diagnosis from maternal blood," *Am. J. Obstet. Gynecol.* 166(5):1350–1355.

Hall et al., 1992, Prenatal and Perinatal Genetics, "Isolation and Purification of CD34 + Fetal Cells From Maternal Blood," *Am. J. Hum. Genet.* 51:A257, Excerpt 1013.

Harrison et al., 1992, Prenatal and Perinatal Genetics, "Use of fluorescence in situ hybridization to detect confined placental mosaicism in trisomic conceptions," *Am. J. Hum. Genet.* 51:A257, Excerpt 1014.

Holzgreve et al., 1992, "Fetal Cells in the Maternal Circulation," *J. Reprod. Med.* 37(5):410–418.

Ikuta et al., 1992, "Lymphocyte Development From Stem Cells", *Ann. Rev. Immunol.* 10:759–83.

Julien et al., 1992, Session 34: Prenatal and Perinatal Genetics II, and Molecular Applications in Clinical Genetics III, "Fetal cells in maternal blood," *Am. J. Hum. Genet.* 51:A48, Excerpt 181.

Lebkowski et al., 1992, "Rapid Isolation of Human CD34 Hematopoietic Stem Cells Purging of Human Tumor Cells", *Transplantation* 53(5):1011–1019.

Russo et al., 1992, *The Use of Resealed Erythrocytes as Carrier's and Bioreactors,* Published by Magnani & DeLoach, Plenun Press, New York, pp. 101–107.

Pope et al., 1993, "New Application of Silane Coupling Agents for Covalenty Binding Antibodies to Glass and Cellulose Solid Supports," *Bioconjugate Chem.* 4:166–171.

Schmitz et al., 1993, "Optimizing follicular dendritic cell isolation by discontinuous gradient centrifugation and use of the magnetic cell sorter (MACS)," *J. of Immunological Methods* 139:189–196.

Simpson et al., 1993, "Isolating Fetal Cells From Maternal Blood, Advances in Prenatal Diagnosis Through Molecular Technology," *Journal of American Medical Association (JAMA)* 270(19):2357–2361.

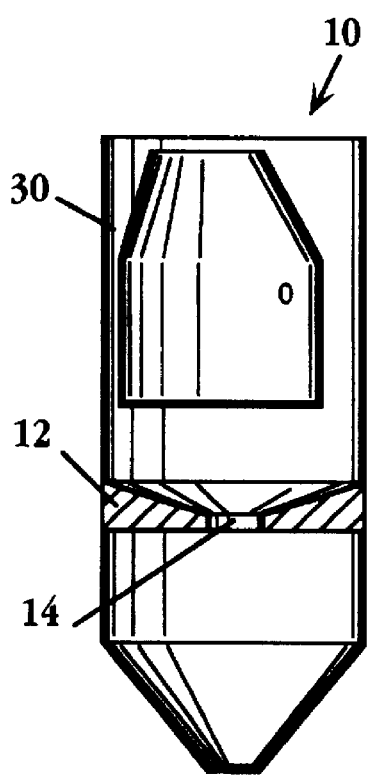 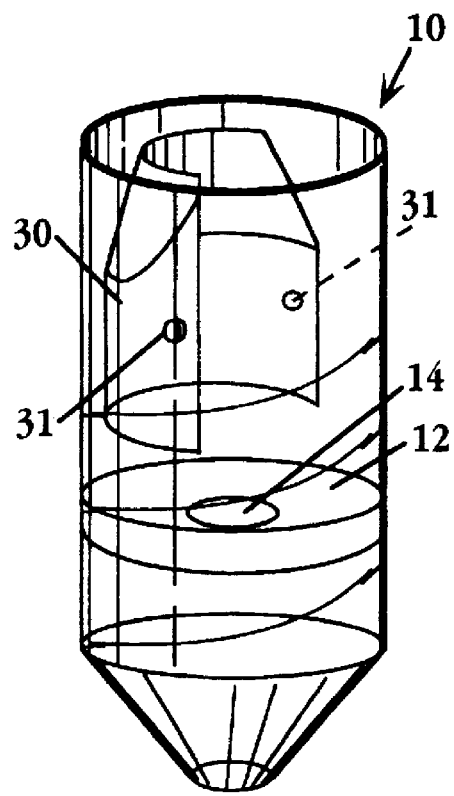
Fig. 2A　　　Fig. 2B
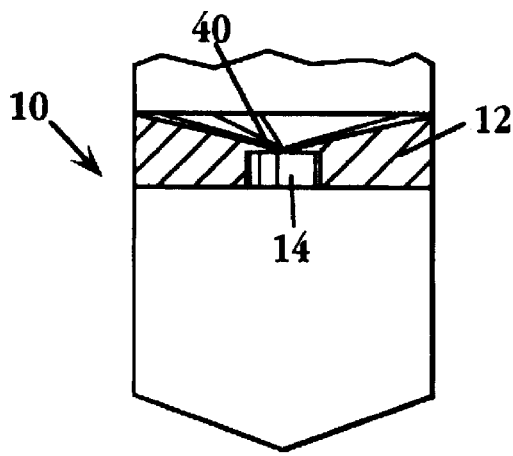
Fig. 3
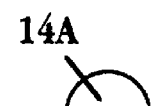
Fig. 4A
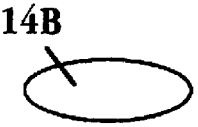
Fig. 4B
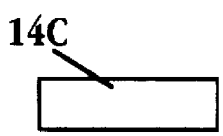
Fig. 4C
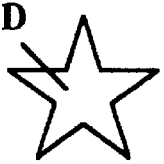
Fig. 4D
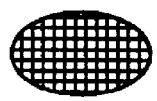
Fig. 4E

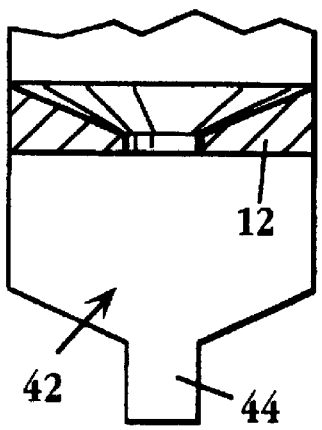 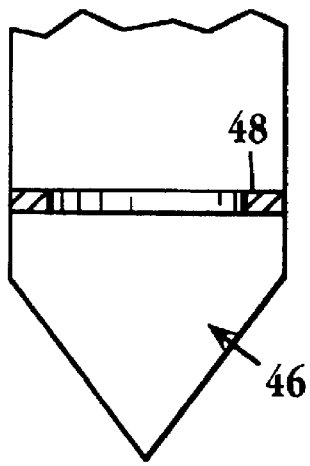 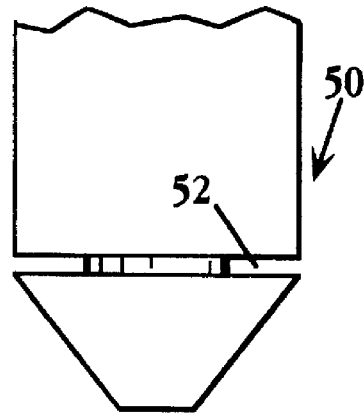
Fig.5A  Fig.5B  Fig.5C
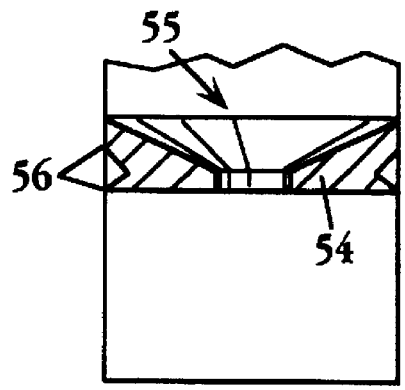 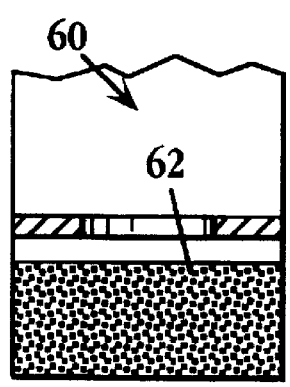 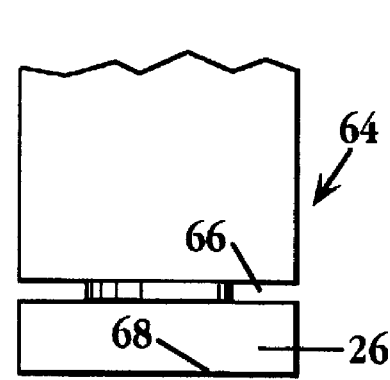
Fig.5D  Fig.5E  Fig.5F
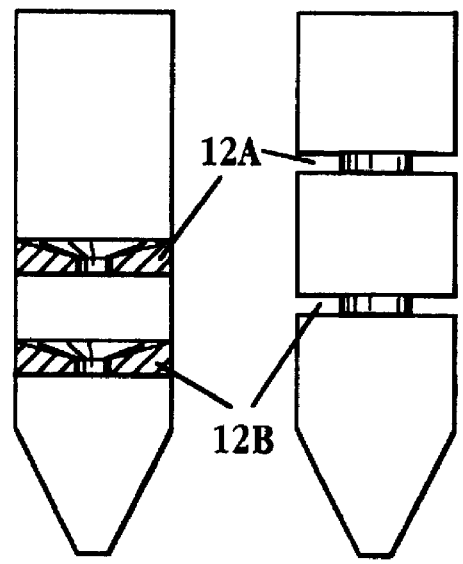 
Fig.6A  Fig.6B

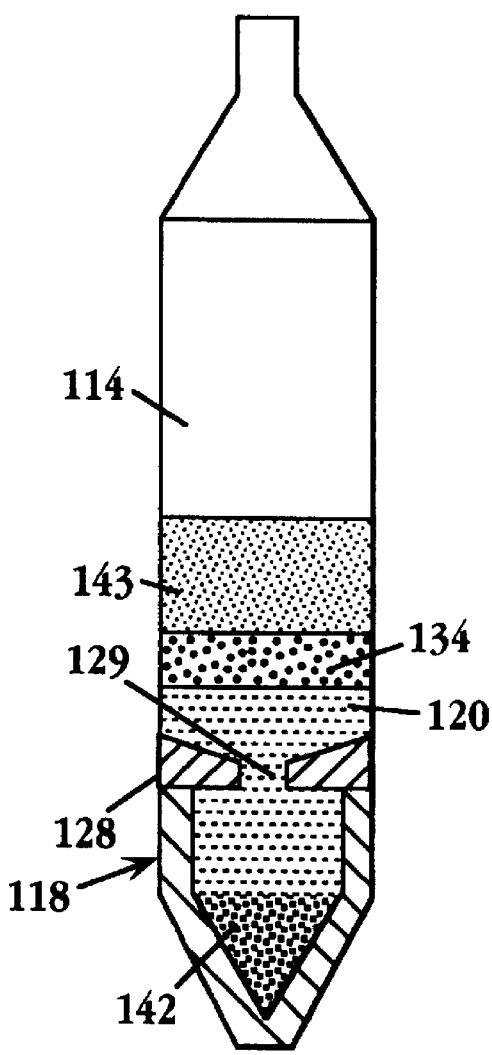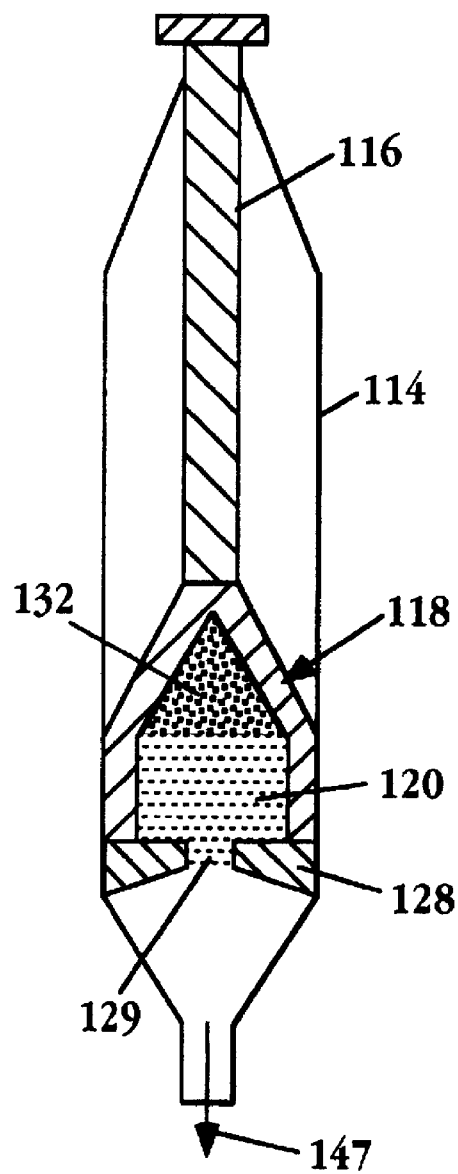

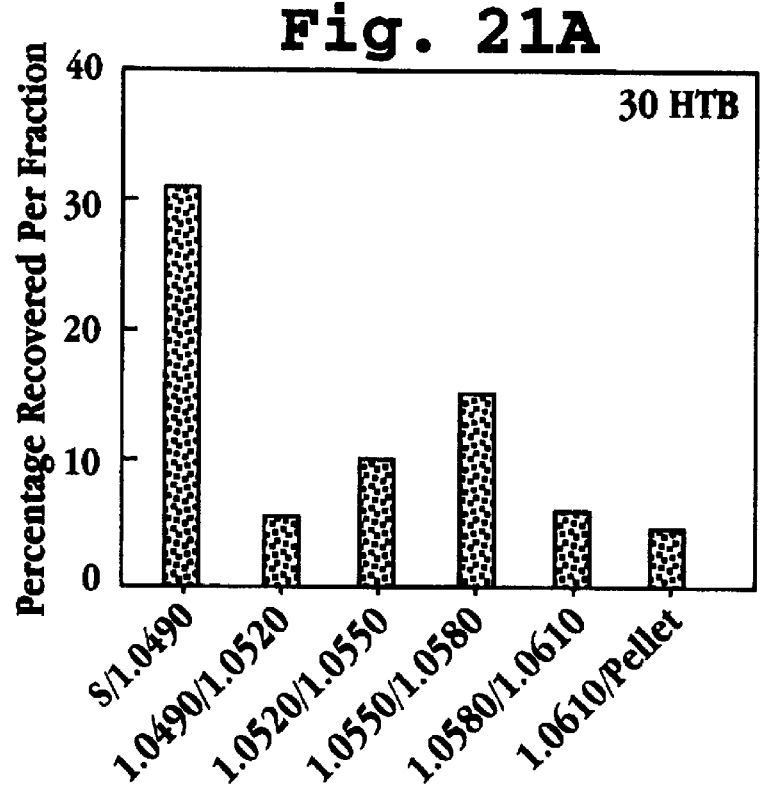
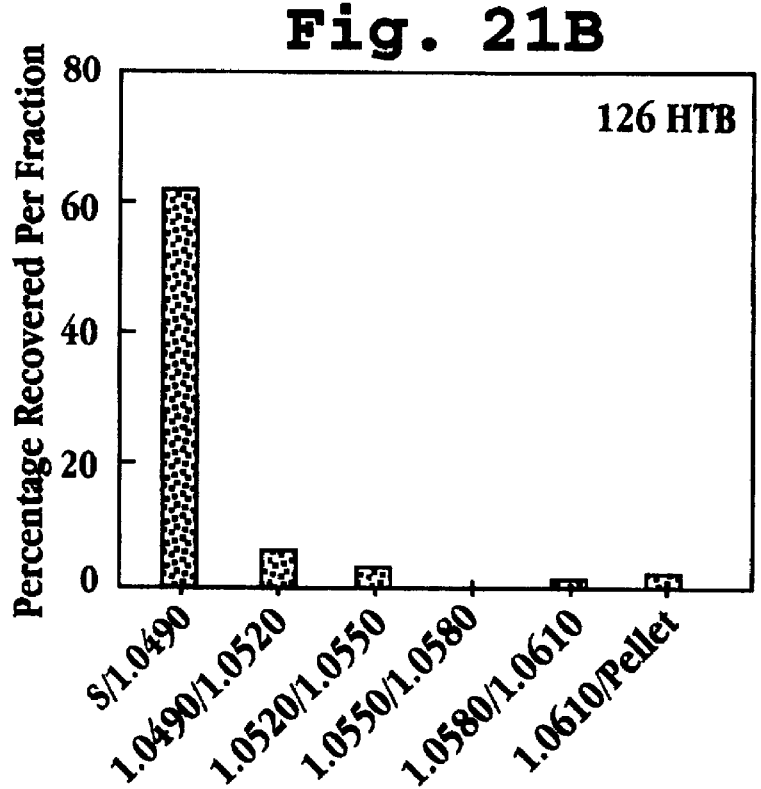

METHODS FOR ENRICHING SPECIFIC CELL-TYPES BY DENSITY GRADIENT CENTRIFUGATION

1. INTRODUCTION

The present invention relates to methods of enriching for a desired cell population from cell sources, such as body fluids, dispersed tissue specimens and cultured cells. In particular, the present invention relates to the use of a cell-trap centrifugation tube containing a specific density gradient solution adjusted to the specific density of a desired cell population to enrich for the desired cell from a cell source. The tube allows the desired cell population to be collected by decantation after centrifugation to minimize cell loss and maximize efficiency. In addition, the method can be further simplified by density-adjusted cell sorting which uses cell type-specific binding agents such as antibodies, lectins, peptides and growth factors linked to carrier particles to impart a different density to the undesired populations in a more convenient manner. The rapid cell enrichment method described herein has a wide range of diagnostic and therapeutic applications.

2. BACKGROUND OF THE INVENTION

Separating components of biological fluids and tissues is often desirable for clinical diagnostic and therapeutic applications. In the clinical diagnostics field, there is a need, for example, for morphological analysis of tumor cells, fetal karyotyping, and tissue typing procedures. Therapeutically, there is a need, for example, for purging cells or tissues intended for use in autologous cellular or tissue transfusions or transplantations, e.g. purging tissues of viral antigens and tumor cells. There is also a need for enriching or isolating desirable cells for use in transplantations, e.g. for use in ex vivo expansion of hematopoietic cells intended for allogeneic and autologous transplantation.

Several methods are known in the art for separating desirable cells from body fluids. Such methods include separating cells based upon buoyant density in a cell separation composition (U.S. Pat. No. 4,927,750), separating serological factors on density gradients using latex beads coated with anti-serological factor (U.S. Pat. No. 3,862,303), separating cells through the use of a magnetic field (U.S. Pat. No. 4,777,145), and separating T and B cells on density gradients (U.S. Pat. No. 4,511,662). Cell separation methods known in the art may have the disadvantage of cell loss due to the sticking of cells to tubes and pipettes.

The present invention provides the advantage of enriching for minor populations of desirable cells from cell sources or mixtures containing multiple cell populations and collecting the enriched cells in a high yield and efficient manner through the use of the cell-trap centrifuge tube. The present invention further provides the advantage of high specificity separation through the use of the density adjusted cell sorting procedure method.

3. SUMMARY OF THE INVENTION

The present invention relates to methods of isolating and enriching for a desired cell population from cell sources, such as body fluids, dispersed tissue specimens and cultured cells in a rapid and high yield manner.

The invention is based, in part, on Applicant's discovery that a "PERCOLL" gradient solution adjusted to the density of the desired cell population with an accuracy of ±0.0005 to ±0.0002 gr/ml, efficiently separates desired cell populations from undesired cell populations without prior separation if overlaid on the gradient solution. In addition, the method is improved by using cell-trap centrifugation tubes described herein which contain a constriction that allows the high yield and efficient separation of cells. The efficiency of the method is further improved when it is combined with the use of cell type-specific binding agents, directly or indirectly bound, to carrier particles allowing for affinity separation of the desired cell population or the non-desired cell population. This method is hereinafter referred to as density adjusted cell sorting.

In one embodiment described herein, the invention provides for a rapid and high yield single-step procedure to isolate breast tumor cells from a cell source or cell mixture. The increased number of breast tumor cells in the enriched cell population enhances the sensitivity and accuracy of diagnosis.

In another embodiment described herein, the invention provides for a rapid and high yield single-step procedure to isolate hematopoietic stem cells from a cell source or cell mixture.

In yet another embodiment described herein, the invention provides for a rapid and high-yield single-step procedure to enrich fetal cells from maternal body fluids.

In yet another embodiment described herein, the invention provides a cell trap centrifugation tube or centrifugation syringe which contains a constriction that allows for the high yield and efficient separation of desired cell populations.

The method of the present invention also provides for the determination of the density of any given cell type accurate to within ±0.0005 gr/ml and preferably within ±0.0002 gr/ml of the specific gravity of the desired cell based upon the use of serial density gradients.

4. BRIEF DESCRIPTION OF THE DRAWINGS

Figure 1B:
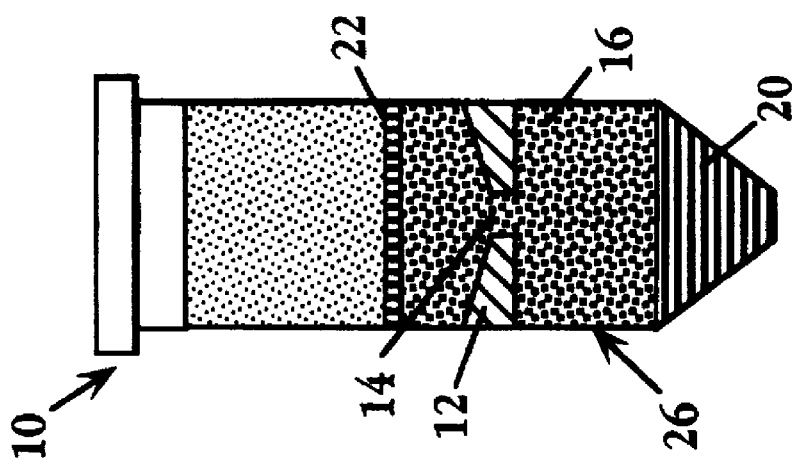
Figure 1A:
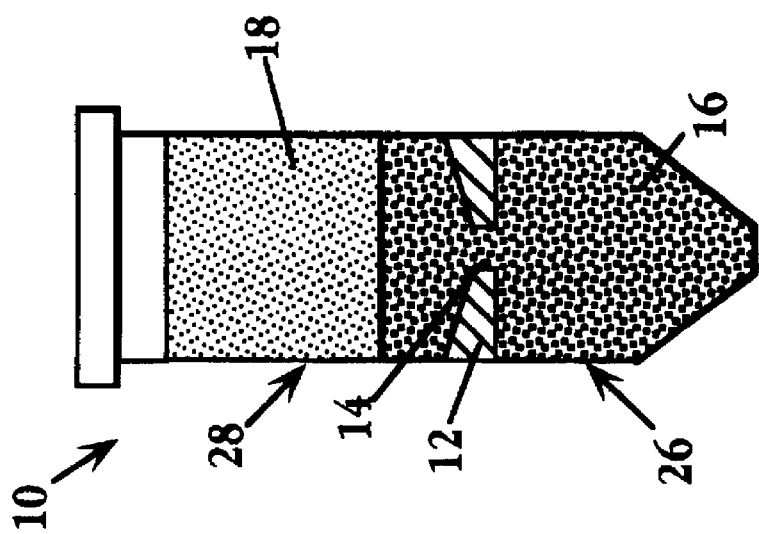

FIGS. 1A–C Cross-sectional views of a preferred embodiment of the centrifugation tube according to the present invention, illustrating the steps of isolating or separating cells according to the invention.

FIG. 2A A schematic cross-sectional view of an alternative preferred embodiment of the present invention.

FIG. 2B A perspective view of the embodiment of FIG. 2A.

FIG. 3 A cross-sectional view of an alternative embodiment of the constriction member of the invention with a valve.

FIGS. 4A–E Examples of alterative shapes of the opening in the constriction member.

FIGS. 5A–F Cross-sectional views of alternative embodiments of the tube and constriction member of the invention.

FIGS. 6A and 6B Cross-sectional views of further alternative embodiments of the invention having multiple constriction members.

Figure 7:
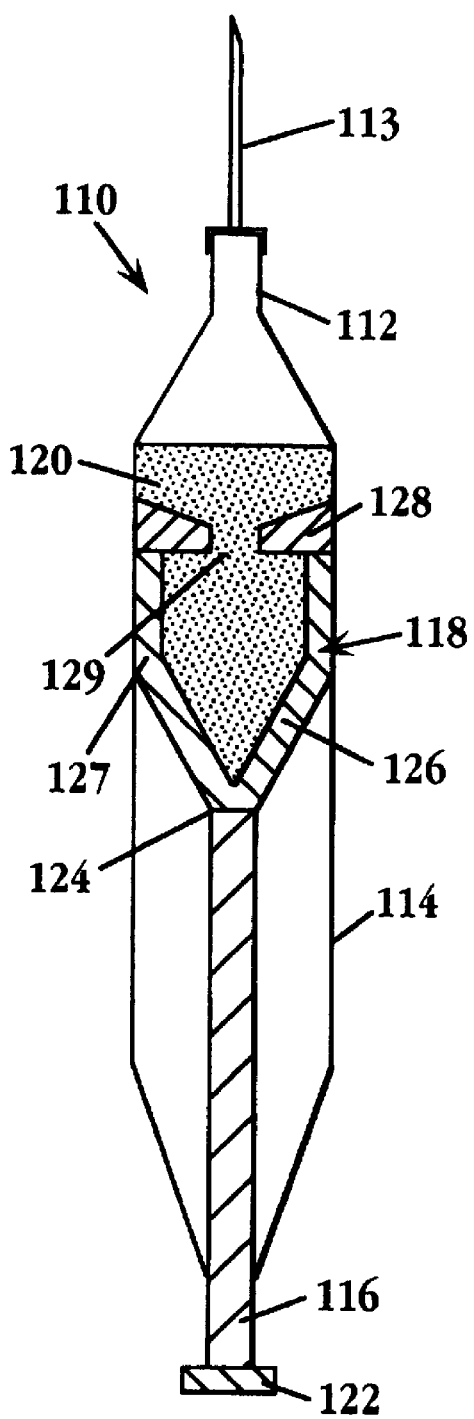

FIG. 7 A cross-sectional view of a centrifuge syringe before the extraction of a specimen.

Figure 8:
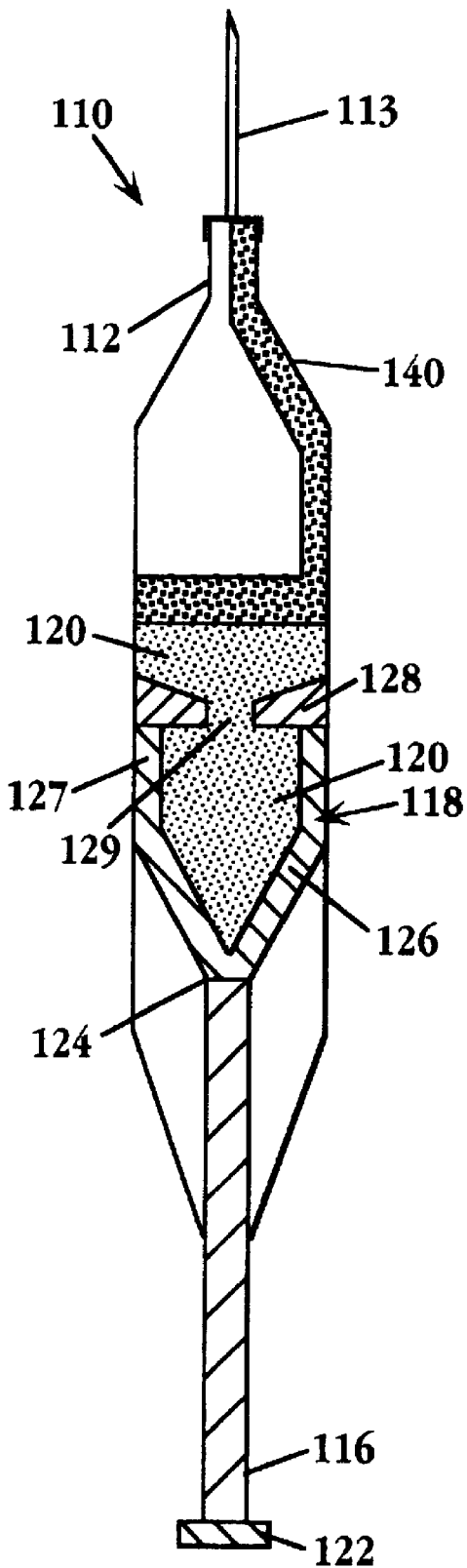

FIG. 8 A cross-sectional view of the centrifuge syringe of FIG. 7 upon introduction of the specimen.

FIG. 9 A cross-sectional view of the centrifuge syringe of FIG. 7 after centrifugation.

FIG. 10 A cross-sectional view of the centrifuge syringe of FIG. 7 upon removal of the specimen.

FIGS. 11A–11D A schematic drawing demonstrating the density adjusted cell sorting procedure.

Figure 12A:
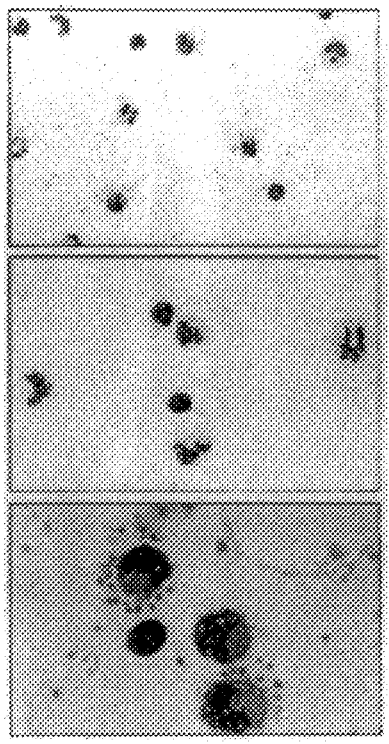
Figure 12B:
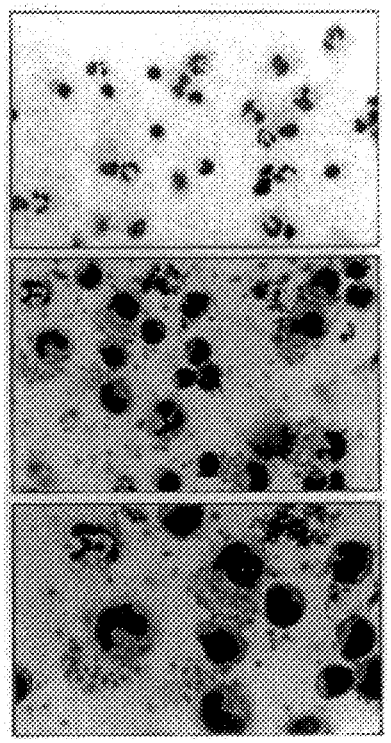
Figure 12C:
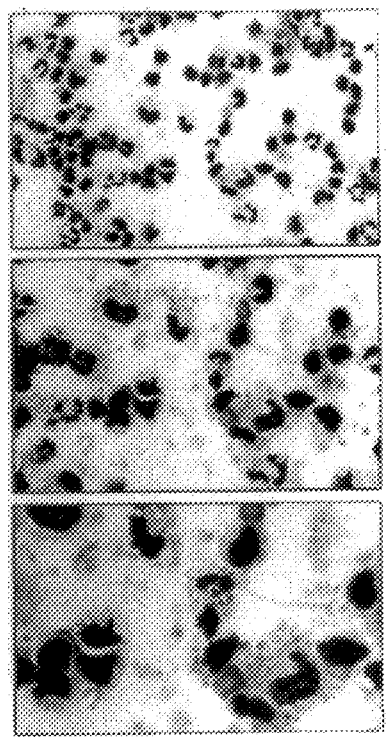

FIGS. 12A–12C A comparison of cell numbers in three cell preparations isolated by the conventional method using "FICOLL" as the density material (FIG. 12A), "FICOLL" plus cell-trap tubes (FIG. 12B), and adjusted "PERCOLL" density gradient plus cell-trap tubes (12C).

Figure 13A:
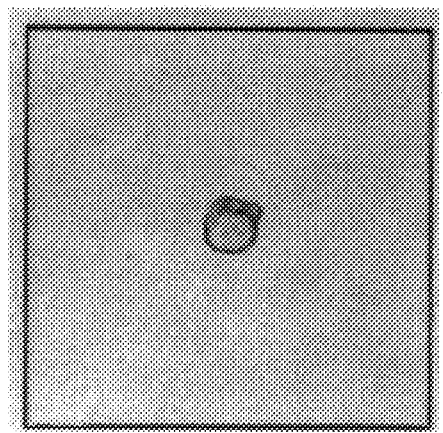
Figure 13B:
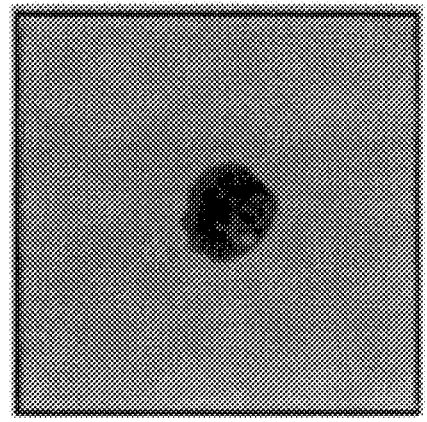
Figure 13C:
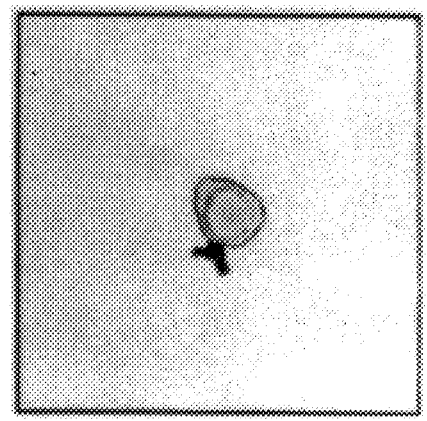

FIGS. 13A–13C An identification of nucleated red blood cells isolated by "PERCOLL" centrifugation in cell-trap tubes followed by anti-CD45 depletion.

Figure 14:
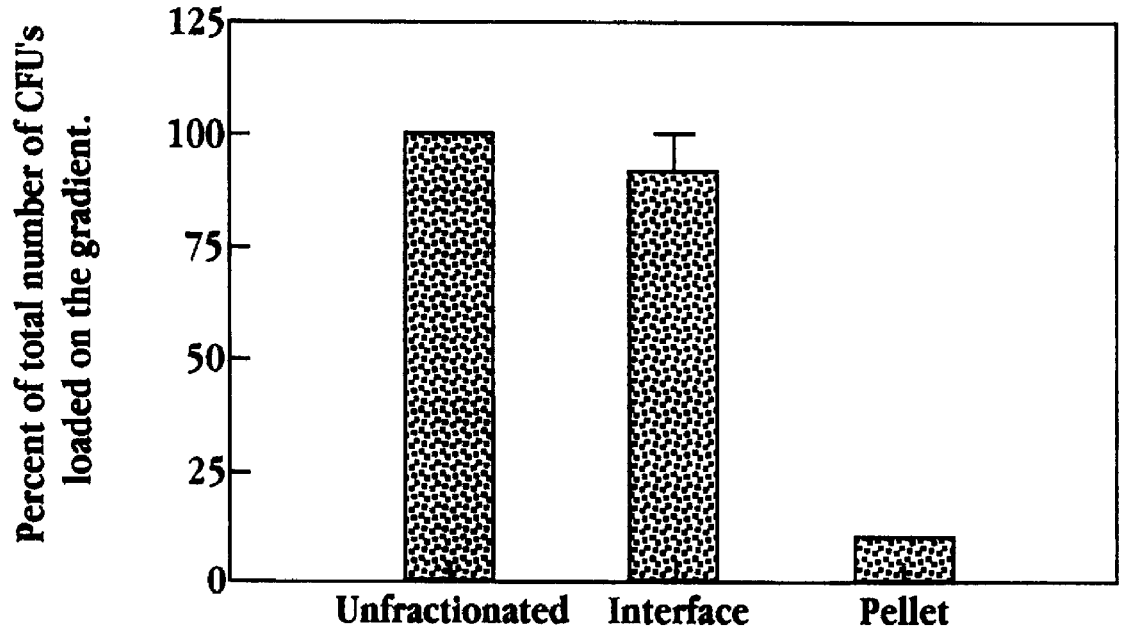

FIG. 14 Distribution of CFU's in interface and pellet fractions.

Figure 15:
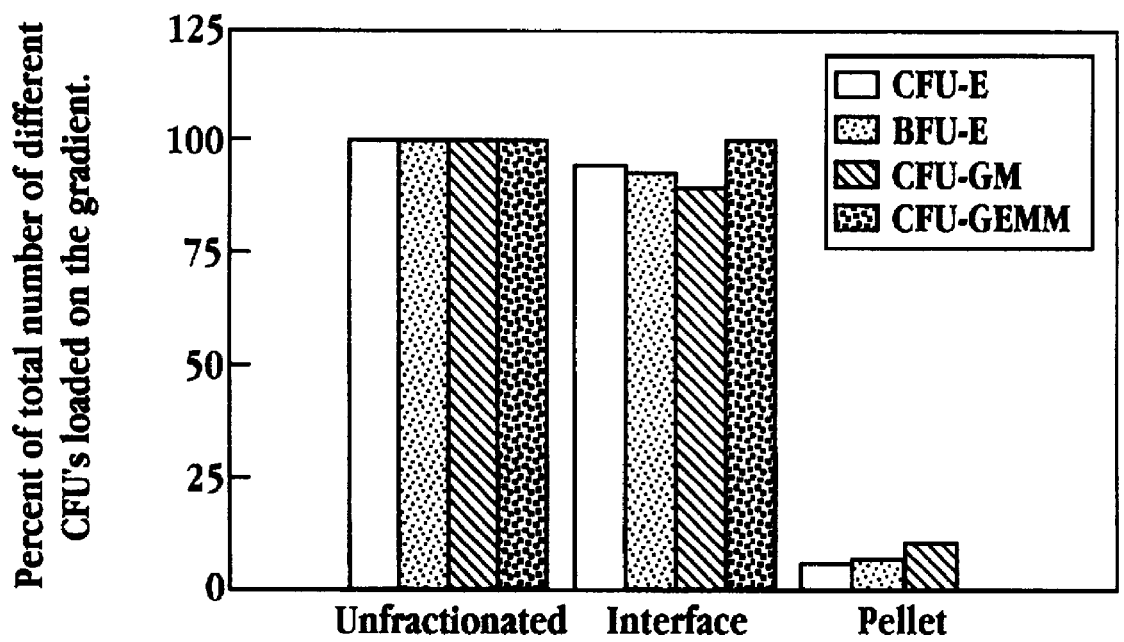

FIG. 15 Distribution of different types of CFU's in interface and pellet fractions.

Figure 16:
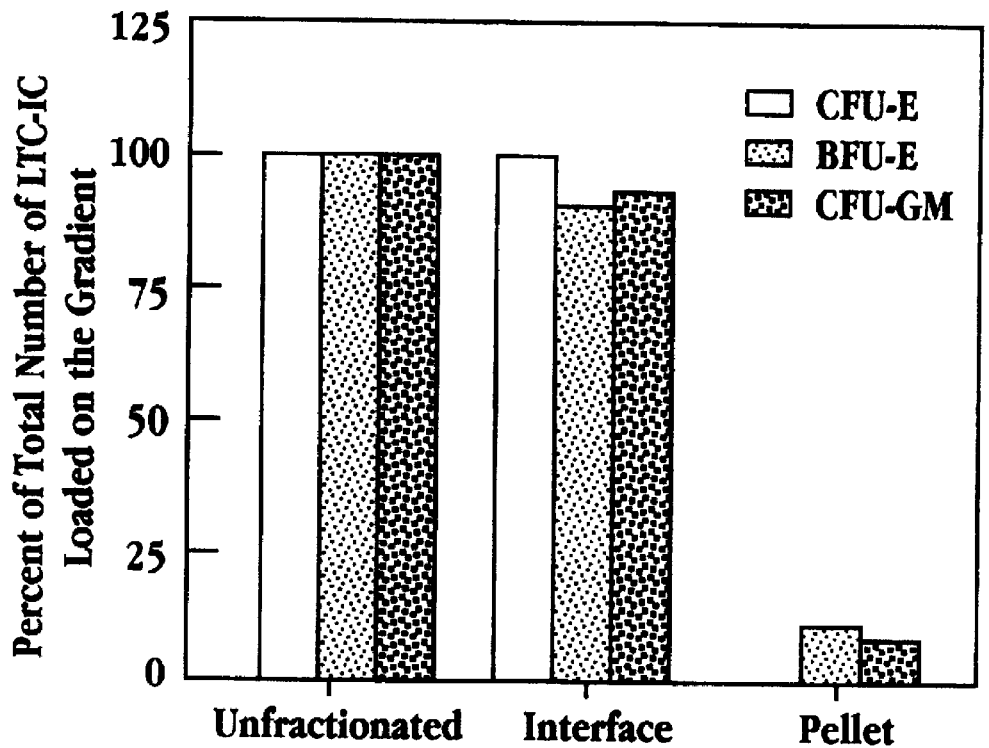

FIG. 16 Distribution of long-term culture initiating capability in interface and pellet fractions.

Figure 17:
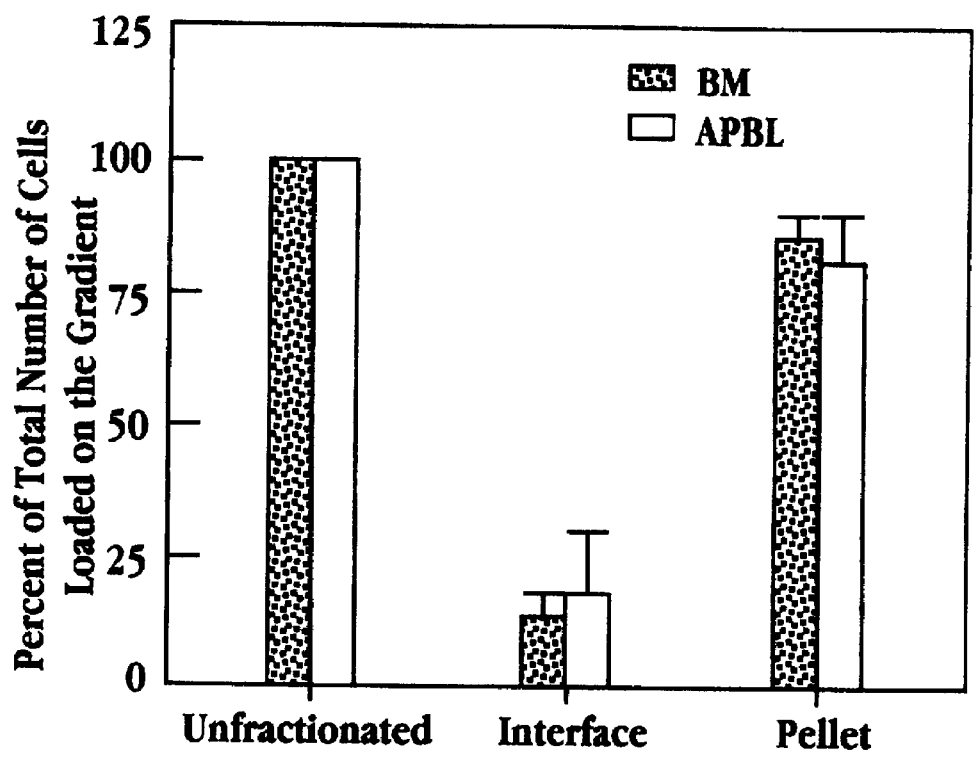

FIG. 17 Distribution of T cells in interface and pellet fractions.

Figure 18:
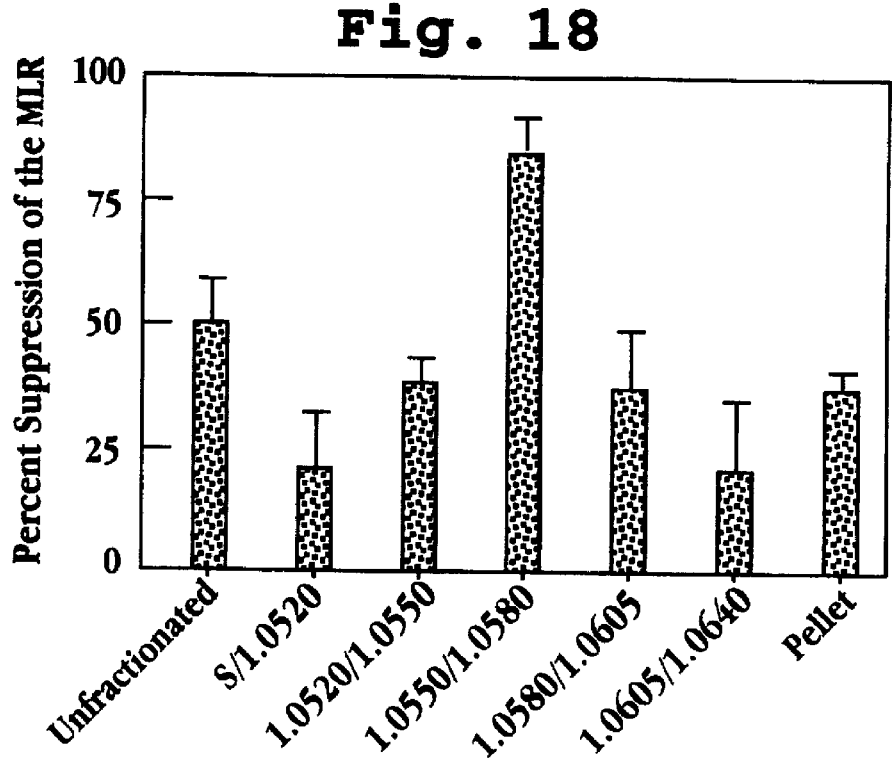

FIG. 18 Distribution of natural suppressor activity in different density fractions.

Figure 19:
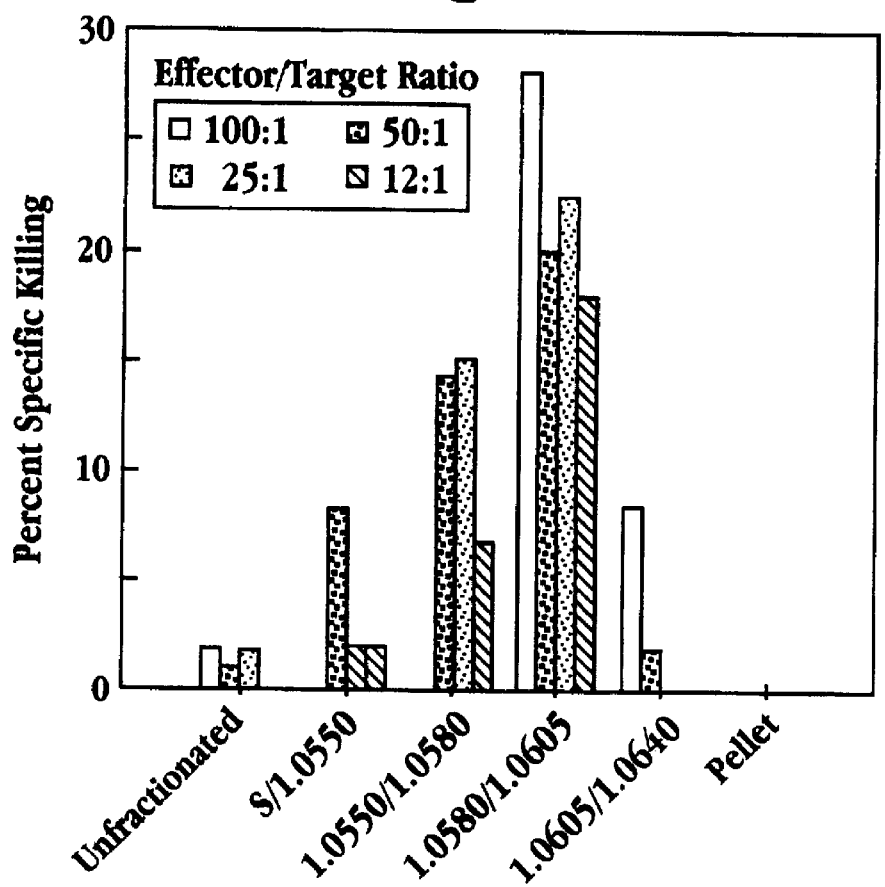
Figure 20A:
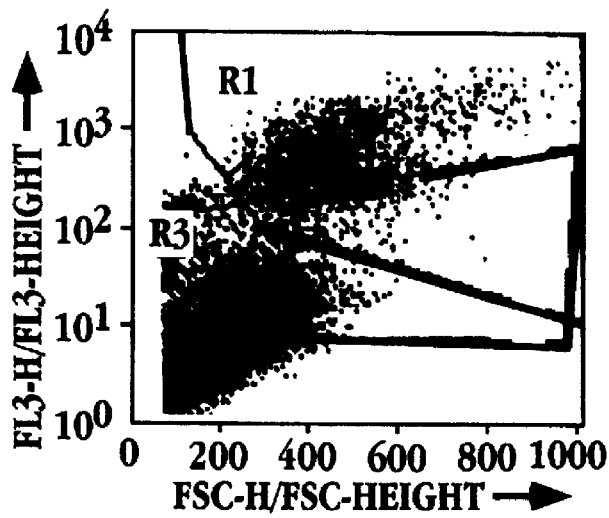
Figure 20D:
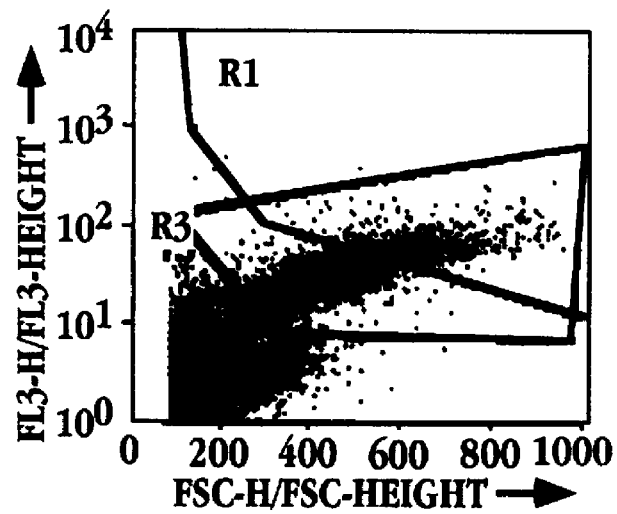
Figure 20B:
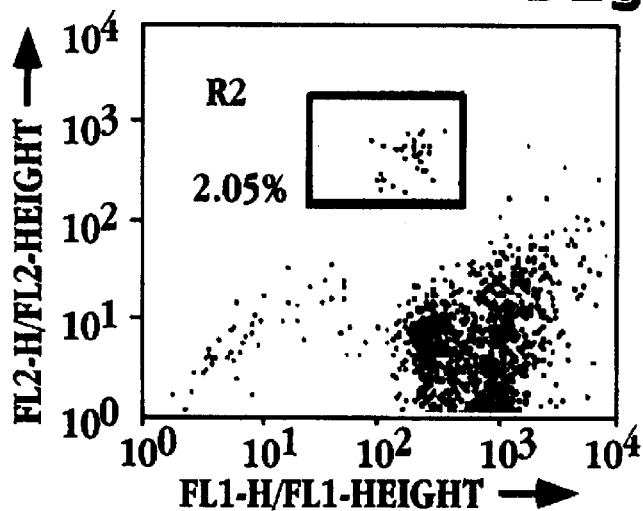
Figure 20E:
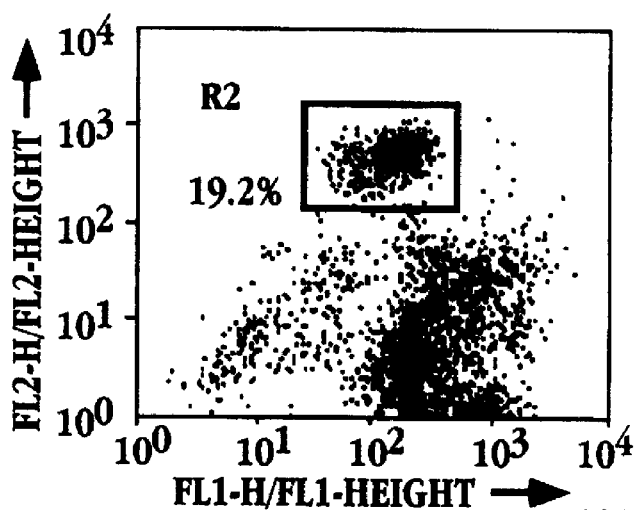
Figure 20C:
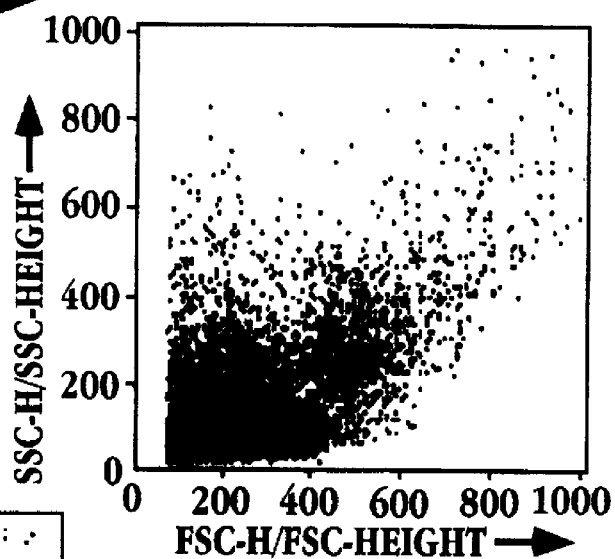
Figure 20F:
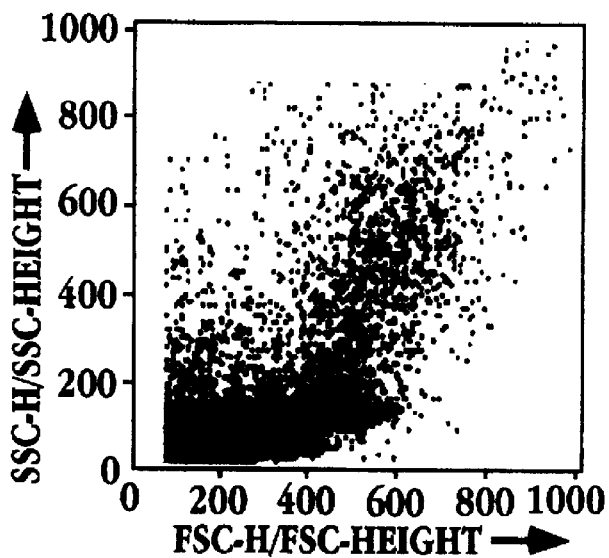
Figure 21C:
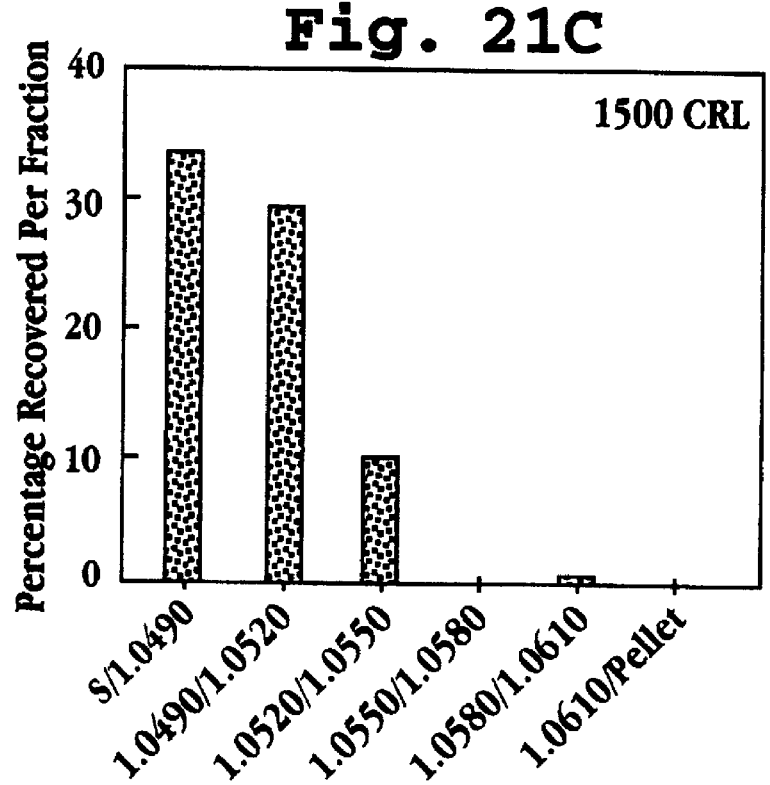
Figure 21D:
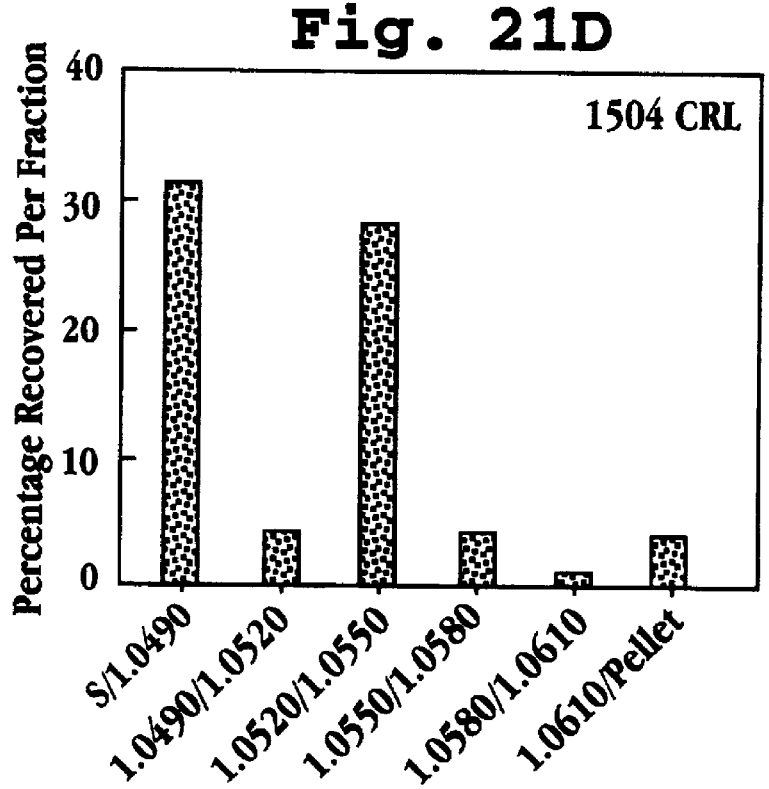
Figure 22A:
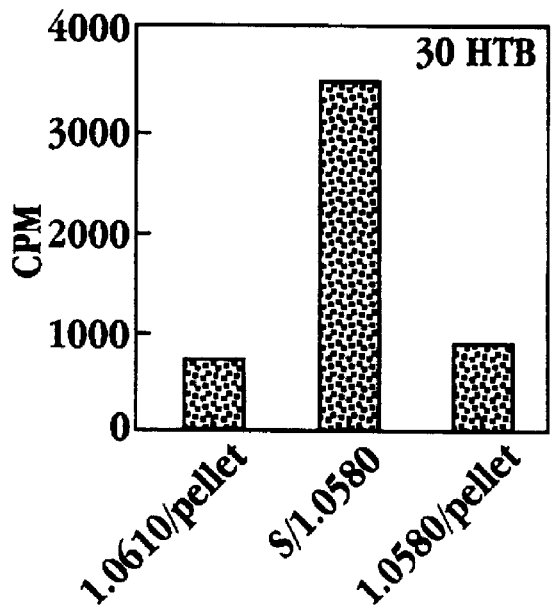
Figure 22B:
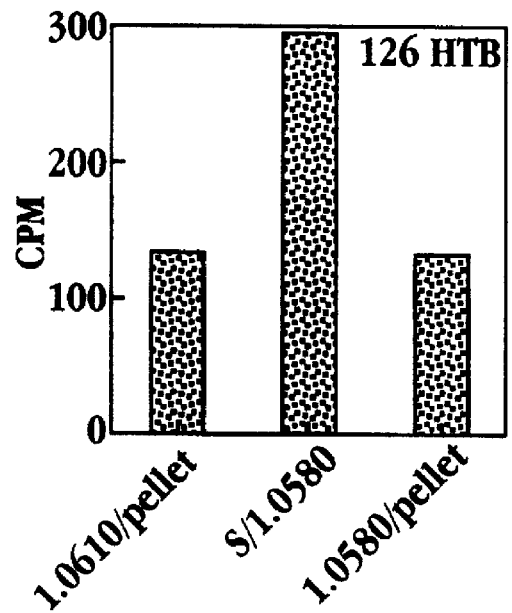
Figure 22C:
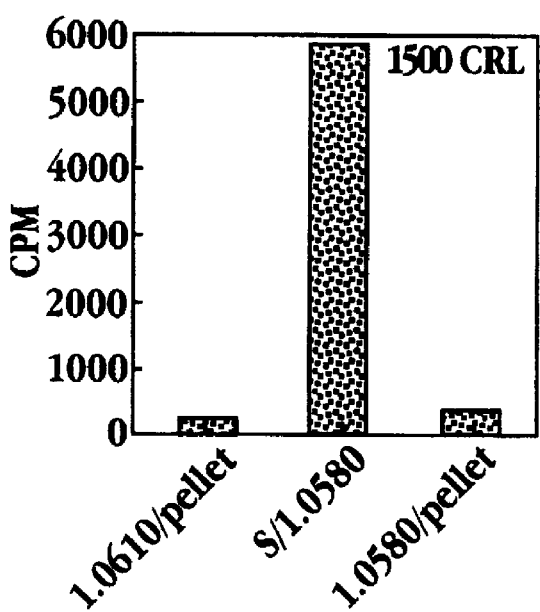
Figure 22D:
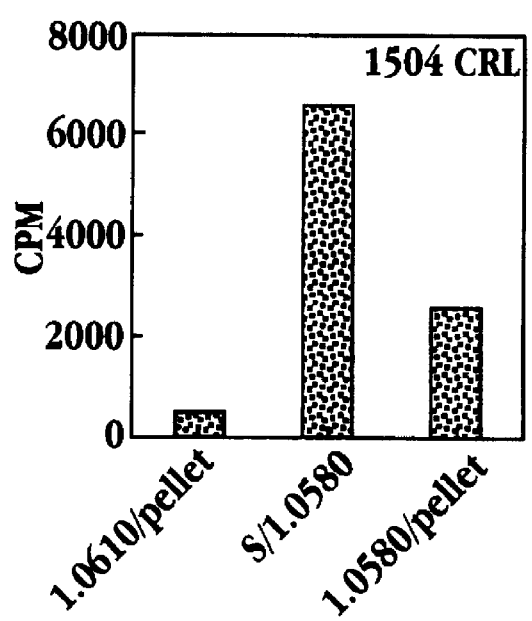

FIG. 19 Distribution of natural killer activity in different density fractions.

FIGS 20A–20F Flow cytometric analysis of $CD34^+$ cell enrichment after density gradient centrifugation plus density adjusted cell sorting.

FIGS. 21A–21D Enrichment of 4 breast tumor cell lines using the cell separation method of the present invention.

FIG. 22A–22D Illustration that the ideal density for enrichment of breast tumor cells spiked in a cell mixture is 1.0580.

5. DETAILED DESCRIPTION OF THE INVENTION

The present invention relates to methods of rapid and high yield isolation or enrichment of a desired cell population from body fluids, dispersed tissue specimens, cultured cells and their components, based on density gradient centrifugation. More specifically, the present invention relates to the use of a specially designed cell-trap centrifugation tube containing a precisely determined density of a density gradient solution and a manner of collecting the desired cell population which maximizes yield.

The cell separation method of t he present invention may be used, for example, to enrich fetal cells from circulating maternal blood for the purpose of performing a variety of genetic analysis, e.g. karyotyping; to enrich tumor cells from circulating blood for the purpose of performing diagnostic tests, e.g. cytological examination, or for the purpose of purging tumor cells from a blood sample intended for subsequent re-infusion, e.g. transfusions or transplants; to enrich morula or blastocyst stage cells from reproductive fluid samples for use in in vitro fertilization; to enrich for islet of Langerhans cells from a dispersed tissue sample for transplantation purposes; or to enrich hematopoietic progenitor cells from the blood or bone marrow for use as donor cells in bone marrow transplantation.

5.1. DIVERSE CELL TYPES MAY BE ENRICHED BY THE PRESENT INVENTION

The cell separation method of the present invention may be used to isolate or enrich for any desired cell population from in vivo or in vitro sources including, but not limited to, body fluids, e.g. circulating and umbilical cord blood, urine, semen, bone marrow, amniotic fluid, spinal and pleural fluids, ascites, sputum; tissue specimens, including adult and fetal tissue samples; and cultured cells. Examples of desired cell populations include, but are not limited to, cells of the reproductive system, e.g. oocytes, spermatozoa, leydig cells, embryonic stem cells, amniocytes, blastocysts, morulas, and zygotes; leukocytes, e.g. peripheral blood leukocytes, spleen leukocytes, lymph node leukocytes, hybridoma cells, T cells (cytotoxic/suppressor, helper, memory, naive, and primed), B cells (memory and naive), monocytes, macrophages, granulocytes (basophils, eosinophils, and neutrophils), natural killer cells, natural suppressor cells, thymocytes, and dendritic cells; cells of the hematopoietic system, e.g. hematopoietic stem cells (CD34+), proerythroblasts, normoblasts, promyelocytes, reticulocytes, erythrocytes, pre-erythrocytes, myeloblasts, erythroblasts, megakaryocytes, B cell progenitors, T cell progenitors, thymocytes, macrophages, mast cells, and thrombocytes; stromal cells, e.g. adipocytes, fibroblasts, adventitial reticular cells, endothelial cells, undifferentiated mesenchymal cells, epithelial cells including squamous, cuboid, columnar, squamous keratinized, and squamous non-keratinized cells, and pericytes; cells of the skeleton and musculature, e.g. myocytes (heart, striated, and smooth), osteoblasts, osteoclasts, osteocytes, synoviocytes, chondroblasts, chondrocytes, endochondral fibroblasts, and perichonondrial fibroblasts; cells of the neural system, e.g. astrocytes (protoplasmic and fibrous), microglia, oligodendrocytes, and neurons; cells of the digestive tract, e.g. parietal, zymogenic, argentaffin cells of the duodenum, polypeptide-producing endocrine cells (APUD), islets of langerhans (alpha, beta, and delta), hepatocytes, and kupfer cells; cells of the skin, e.g. keratinocytes, langerhans, and melanocytes; cells of the pituitary and hypothalamus, e.g. somatotropic, mammotropic, gonadotropic, thyrotropic, corticotropin, and melanotropic cells; cells of the adrenals and other endocrine glands, e.g. thyroid cells (C cells and epithelial cells); adrenal cells; and tumor cells.

For purposes of improved tumor detection and tumor cell purging from cell mixtures for allogeneic and autologous bone marrow transplantation, it may be desirable to isolate a variety of tumor cells using tumor cell antigens or antibodies to tumor cell antigens which are commercially available or known to those of skill in the art including, but not limited to, tumors such as epithelioid carcinoma of the cervix, larynx and of oral origin; Burkitt lymphoma cells, choriocarcinoma cells, adenocarcinoma cells; non Hodgkin's B and T cell lymphoma cells, fibrosarcoma cells, neuroblastoma cells, plasmacytoma cells, rhabdomyosarcoma cells, carcinoma cells of the pharynx, renal adenocarcinoma, hepatoma cells, fibrosarcoma cells, myeloma cells, osteosarcoma cells, teratoma cells, teratomal keratinocytes, lung carcinoma cells, colon adenocarcinoma cells, lung adenoma cells, renal carcinoma cells, rectum adenocarcinoma cells, chronic myelogenous leukemia cells, ileocecal adenocarcinoma cells, hairy cell leukemia cells, acute myelogenous leukemia cells, colon carcinoma cells, cecum carcinoma and adenocarcinoma cells, leukemia-cecum adenocarcinoma cells, pancreatic carcinoma, Wilm's tumor cells, prostate adenocarcinoma cells, renal leimyooblastoma cells, bladder carcinoma cells, plasmacytoma cells, teratocarcinoma cells, breast carcinoma, epidermoid carcinoma of the cervix, ovarian teratocarcinoma, myeloma cells, T and B cell lymphoma cells, amalanotic melanoma cells, cervical carcinoma cells, rhabdomyosarcoma, hepatoma, medullary Thyroid carcinoma cells, malignant melanoma cells, glioblastoma cells, plasma cell leukemia, endometrial adenocarcinoma, squamous cell carcinoma, pancreatic adenocarcinoma, astrocytoma, gastric adenocarcinoma, pulmonary mucoepidermoid carcinoma cells, myeloid leukemia cells, EBV-transformed B cells, renal cell adenocarcinoma, acute leukemia, B cell plasmacytoma, acute lymphocytic leukemia, cutaneous T lymphoma, T cell leukemia, acute lymphoblastic leukemia, HIV+ T cells, medulloblastoma, B cells from sickle cell disease, acute monocytic leukemia, adrenocortical carcinoma, Bowes Melanoma and hepatocellular carcinoma. Leukocyte differentiation antigens are described in *Leucocyte Typing IV, White Cell Differentiation Antigens* 1989, ed. Knapp et al., pub. Oxford University Press, specifically incorporated herein in its entirety.

It may also be desirable to isolate or enrich for a variety of tumor markers, which occur in sites where the tumor cells are not normally found (e.g. epithelial specific cytokeratins in the peripheral blood) known to be associated with disease by using antibodies to tumor markers as cell type-specific binding agents in the density adjusted cell sorting procedure. A variety of tumor markers are known in the art or are commercially available and include, but are not limited to tumor-associated antigen HER-2/neu (Beckmann et al., 1992, *Eur. J. Cancer* 28:322) associated with human breast and gynecological cancers; TA-4 (Kato et al., 1977), human papilloma virus (HPV) and cytokeratins (Moll et al., 1982), associated with cervical cancer; cancer antigen 19-9 (CA 19-9) (Koprowski et al., 1981), CA 50 (Lindholm et al., 1983), CA 195 (Bray et al., 1987), carcinoembryonic antigen (CEA) (Gold et al., 1965) and DU-PAN-2 (Metzger et al., 1981) associated with cancer of the pancreas; CA 15-3 (Kufe et al., 1984), CA 549 (Bray et al., 1987), cathepsin D (Westley et al., 1980), EGF-R (Osborne et al., 1980), estrogen receptor (Gorski et al., 1966), Ki-67 (Gerdes et al., 1983), progesterone receptor (Horowitz et al., 1983), and TGF-α, associated with breast cancer; retinoblastoma gene product (Friend et al., 1986), associated with cancer of the eye; TAG-72 (Johnson et al., 1986), tissue polypeptide antigen (Bjorklund et al., 1954), ras (Parada et al., 1982), and myc (Dalla-Favera et al., 1982) associated with lung cancer; prostate-specific antigen (Wang et al., 1977) associated with prostate cancer; gp75/brown (Brichard et al., 1993, *J. Exp. Med.* 178:489 associated with melanoma; gangliosides (GM2,GD2) (Lloyd, 1991, *Seminars in Cancer Biology* 2:421) associated with melanoma; melanotransferrin (Real et al., 1984, *J. Exp. Med.* 160:1219); p53, nonmutant (Schlichtholz, 1992, *Cancer Res.* 52:6380) associated with breast tumors; T, Tn, sialylTN (Lloyd, 1991, supra) associated with breast tumors; MAGE-1,3 (van der Bruggen et al., 1991, *Science* 254:1643 and Gaugler et al., 1994, *J. Exp. Med.* 179:921) associated with melanoma, lung, and other cancers; tyrosinase/albino (Kawakami et al., 1994, *J. Exp. Med.*) associated with melanoma; MUC1 (Barnd, 1989, *PNAS USA* 86:7159 and Vijayasaradhi et al., 1990, *J. Exp. Med.* 171:1375) associated with pancrease and breast cancer; Melan-A/MART-1 (Coulie et al., 1994, *J. Exp. Med.* 180:35, Hawakami et al., 1994, *PNAS* 91:3515 and Bakker et al., 1994, *J. Exp. Med.* 179:1005) associated with melanoma; and pMcl17/silver (Kawakami, 1994 *PNAS USA*) associated with melanoma.

The resultant yield of isolated or enriched cells from the cell separation methods of the present invention may be used for diagnostic purposes, e.g. morphological, molecular, biochemical or immunophenotypic assays. For example, DNA may be prepared from the collected cells and subjected to polymerase chain reaction (PCR), the collected cells may be cultured and subjected to karyotyping, or the collected cells may be assessed morphologically. For example, the cell separation methods of the present invention may be used to enrich for bladder tumor cells from urine using antibodies specific for a bladder tumor antigen as the cell type-specific binding agent. The resultant enriched bladder tumor cell population may then be used to perform morphological characterization to determine cell type, thereby avoiding the use of invasive and expensive surgical procedures heretofore relied upon for such a determination. Alternatively, the cell separation methods of the present invention may be used for therapeutic indications, e.g. purging or separating unwanted components, such as tumor cells, viral antigens or undesirable antibodies from body fluids or tissues prior to use in cellular or tissue transfusions or transplantations. The cell separation methods of the present invention may also be used therapeutically to enrich for desired cell populations. For example, specific human cells of hematopoietic origin may be enriched from whole human blood by the cell separation methods of the present invention, subjected to ex vivo expansion, then used for treatment of patients receiving chemotherapy or other therapies which deplete the body of the specific hematopoietic cell.

5.2. DENSITY GRADIENT MATERIALS FOR USE IN THE PRESENT INVENTION

The methods of cell separation of the present invention relate to the use of a cell-trap centrifuge tube containing a density gradient material having a specific gravity between 1.0000 gr/ml and 2.0000 gr/ml, preferably between 1.0300 gr/ml and 1.2000 gr/ml, that is accurate within ±0.0005 gr/ml, preferably ±0.0002 gr/ml of the specific gravity of the desired cell. A variety of commercially available gradient materials may be used to achieve cell isolation based on the defined density of the desired cell population, including, but not limited to, "PERCOLL" (a polyvinylpyrrolidine-coated colloidal silica), available from Pharmacia; "FICOLL HYPAQUE" (a mixture of 3,5-diacetamido-2,4,6-triiodobenzoic acid and a nonionic polymer consisting of sucrose and epichlorohydrin); any sugar solution, e.g. sucrose; dextran; any protein solution, e.g. bovine serum albumin (BSA); iodinated low molecular weight compounds such as Metrizamide and heavy salts, e.g. cesium chloride. The density gradient solution should be prepared and adjusted to a pre-determined density; osmolality, most preferably in the range of 280 to 320 mOsm/kg $H_2O$; and pH, preferably from 6.8 to 7.8, and most preferably 7.4 for maintaining a physiologically isotonic density gradient, prior to their use. The osmolality and pH may vary depending upon the particular conditions under which the density gradient separation method is performed. For example, the temperature at which the samples are maintained and/or centrifuged may necessitate modifications to the osmolality and/or pH of the density gradient material in order to maintain the appropriate density. Such modifications of the osmolality and pH will be apparent to those skilled in the art.

Cells collected from an in vivo source should be subject to separation within a relatively short time after their collection because the density of the cells may change according to their culture, collection or storage conditions. In order to maintain the optimal isolation of desired cells from body fluids, it is preferred that the blood samples are used within 48 hours after their collection. Most preferably, body fluids should be subjected to density gradient centrifugation within several hours after collection. The adjusted gradient solution should be added to a centrifugation tube in a volume sufficient to allow all the cells overlaid on it to separate during centrifugation. For example, a volume of about 20–25 ml of the solution is generally adequate for separating desired cells in 20 ml of whole blood.

"SILAN PERCOLL" (S-Percoll), classified as a colloidal silica, is one preferred density gradient material. S-Percoll is prepared from colloidal silica by reacting and thus blocking the silanol groups with an alkyl trimethoxy silane reagent and has the structural formula:

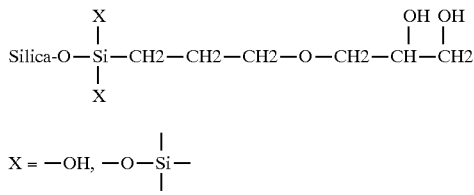

A "PERCOLL" stock solution having osmolality of 280–320 mOs/kg H$_2$O can be made by adding 12 parts of "PERCOLL" with 1 part 10× Ca and Mg free PBS or 1.5M NaCl, for human cells, or adding 9 parts of "PERCOLL" with 1 part 10× Ca and Mg free PBS or 1.5M NaCl, for non-human animal cells.

The methods of cell separation of the present invention require the determination of the density of the desired cell type with an accuracy of ±0.0005 gr/ml, preferably ±0.0002 gr/ml. The density of a given unknown particulate material, may be determined using a series of discontinuous density gradients, each discontinuous density gradient step depending on the exactness of the previous one, or using a continuous density gradient in addition to a discontinuous gradient.

For a discontinuous gradient, a "PERCOLL" stock solution may be prepared as defined infra for the appropriate application. The density of the stock solution up to the fourth digit may be determined using appropriate equipment, for example, a high precision digital density meter such as DMA 48 (Anton PAAR U.S.A., Ashland, Va.) which measures density with an accuracy of ±0.0002 gr/ml. The osmolality of the stock solution may be adjusted appropriately, for example, to 280 mOsm/kg H$_2$O±10 for human use or 320 mOsm/kg H$_2$O±10 for animal use. The pH may be adjusted appropriately, preferentially to 7.4 if a physiologically isotonic solution is desired. The stock "PERCOLL" may be diluted with diluent having the appropriate pH and osmolality and the density may be defined at any time during the procedure using appropriate instrumentation.

For preparation of the first discontinuous density gradient, the following densities of stock "PERCOLL" may be prepared: 1.1250, 1.1150, 1.1050, 1.0950, 1.0850, 1.0750, 1.0650, 1.0550, 1.0450, 1.0350, 1.0250, 1.0150, and 1.0050. The densities should all be accurate to within the range of ±0.0002. The different densities of "PERCOLL" are layered carefully on top of each other using a pipette or a syringe fitted with a wide-bore needle, the heaviest on the bottom and the lightest on the top. The desired particulate matter whose density is to be determined may be layered on the top of the discontinuous density gradient taking care not to mix the particulate material on top of the discontinuous density gradient. The density gradient is centrifuged for 30 minutes at 850 g at room temperature. The particulate material is collected from the different interfaces and defined by it's nature, i.e., morphology, molecular, and biochemical standards or immunophenotypic means. This first discontinuous density gradient allows determination of the density range of the particulate material. For example, if the particulate material is at the interface between 1.0750 and 1.0650, the particulate material is denser than 1.0650 and lighter than 1.0750. A second set of density gradients is prepared with a 0.0010 intervals, for example: 1.0650, 1.0660, 1.0670, 1.0680, 1.0690, 1.0700, 1.0710, 1.0720, 1.0730, 1.0740, and 1.0750, etc. and the process of preparing the gradients performed as described and the centrifugation repeated. The particulate material may be collected from the different interfaces and defined by its nature as described. A third discontinuous density gradient may be prepared based upon the results of the second discontinuous density gradient. For example, if the material of interest is at the interface between densities 1.0700 and 1.0710, this implies that the particulate materials is denser than 1.0700 but lighter than 1.0710. To determine the final working density, the third discontinuous density range may be prepared with density gradient layers having a 0.0005 interval range with intervals being 1.0700, 1.0705, and 1.0710. The fourth digit in this case is accurate to within ±0.0002 which is the limit of detection of the Anton Paar apparatus.

A continuous self-generating density gradient may be prepared using "PERCOLL" which has the characteristic of forming a continuous gradient upon centrifugation at 30,000 g for 15 minutes. Under this condition, the silica particles of different size, forming the stock "PERCOLL", organize such that density changes occur at a microscopic level. A determination of the density range of a particulate material may be performed by layering the material on a pre-formed "PERCOLL" gradient. After the centrifugation, the particulate material may be collected from the gradient and its nature defined as described. The "PERCOLL" stock solution's characteristics can be defined as well. Because it is technically difficult to pull out an individual cell layer without contaminating it with layers above and below, it is preferred to combine the continuous density gradient technique with a series of discontinuous density gradients as described, infra.

Centrifugation in vertical rotors will form gradients of "PERCOLL" rapidly. Care must be taken to ensure that the compacted pellet of "PERCOLL" which may be formed under high speed centrifugation conditions does not contaminate the gradient during collection of the particulate matter of interest. It is not possible to use swing-out type rotors for self-generation of gradients due to the long path length and unequal g-force along the tubes. Zonal rotors can be used to form gradients of "PERCOLL" in situ, the gradients so formed will have the same characteristics as those generated in angle-head rotors. For self-generating gradients, centrifugation should take place at 30,000 g$_{av}$ for 15 minutes. The above-described procedure for determining density may be used to precisely define the specific density of any cell population of interest.

5.3. CELL-TRAP CENTRIFUGATION TUBES FOR USE IN THE PRESENT INVENTION

A centrifugation tube of the present invention includes a constriction and is used in conjunction with a material having defined density as described infra, i.e., a specific density gradient solution having a density accurate to within ±0.0005, and most preferably to within ±0.0002 gr/ml of the desired density. As shown in FIGS. 1A and 1B, tube 10 includes constriction member 12, which defines central opening 14. The upper surface of constriction member 12 is preferably slightly angled inward, toward opening 14. The bottom surface of the constriction member also may be similarly, slightly angled (although not shown as such in the figures). In an exemplary embodiment, with a tube having an inner diameter of about 2.8 cm, the diameter of opening 14 formed by constriction member 12 is preferably about 0.5 cm. The size of opening 14 is generally not so small as to prevent heavier components of a sample, layered on top of the density gradient solution, from passing through the opening prior to actual centrifugation. Such a movement of components may occur due to normal gravitational forces. In general, the diameter of opening 14 is dictated by the ability to form an increased surface tension across the opening. A restriction that is little more than a rim around the interior of the barrel may be sufficient. Hence, the cross-sectional area of the aperture formed by the constriction member may be as little as about 5% or as great as about 95% of the horizontal cross-sectional surface area of the syringe.

Tube 10 is filled with density gradient solution 16 to a level above constriction member 12, or at least above opening 14. Preferably, with reference to a standard 50 ml centrifugation tube, density gradient solution 16 is filled to a level at least about 1 mm above the constriction member. The fluid sample to be separated is layered on the top of the density gradient solution, and the tube and its contents are subjected to centrifugation. Preferably, the sample is carefully layered so that at least about 1 mm of density gradient solution remains between the sample and the top of the constriction member after layering.

Referring to FIG. 1B, following centrifugation, components having densities greater than that of the gradient solution are found in a pellet 20 at the bottom of tube 10. Components having densities less than that of the density gradient solution remain floating at the top of the solution, in an interface 22 between the gradient solution and the remaining portion of the fluid sample solution. The interface portion is then poured off as indicated by arrow 24 in FIG. 1C. The provision of the density gradient solution to a level above the opening as described above helps to prevent the formation of an interface portion below constriction member 12.

Constriction member 12 facilitates pouring off the upper portion by providing a support or nucleus for formation of an intermediate surface tension across the surface of opening 14 when tilted for pouring. This surface tension impedes mixing of upper and lower regions of the tube when the contents of the upper region are poured out of the tube. Constriction member 12 may be provided as an insert placed into a straight-walled tube. Alternatively, constriction member 12 may be formed as constriction of the tube wall during a molding process in the making of the tube itself.

When the constriction member is provided by an insert, the insert may be movable to enable the operator to change the relative volumes of the lower portion 26 and upper portion 28 of tube 10 according to experimental conditions. The position of the constriction member in a molded tube can also be varied, during the manufacturing process, to provide tubes of differing relative upper and lower portion volumes. For example, in the isolation of cells from peripheral blood, a 20 ml sample of blood requires lower portion 26 to be about 15 ml in order to accommodate the relatively large amount of red blood cells centrifuged out. By comparison, a 20 ml sample of apheresis or buffy-coat blood would require only about 10 ml in the lower portion.

In many applications, it will be desirable to collect only the supernatant fraction containing the interface portion. In such cases, the pellet is discarded with the tube. In other cases, the pellet can be removed by mechanical manipulation/disruption. For example, the tube can be inverted and subjected to vortex mixing. Such mixing will disrupt the pellet into the adjacent liquid phase and will induce movement of this liquid phase and disrupted cells from the lower or collection portion of the tube into the upper portion of the tube.

An advantage of the present invention is that the low density material above the constriction member is separated from material beneath by the simple act of pouring. This contrasts with many conventional methods of unloading gradient separations using standard straight-wall centrifuge tubes, where materials are separated by carefully pipetting out of the tube or, alternatively, by puncturing the bottom of the tube and allowing the contents of the tube to slowly drip out into collection vessels. Thus, the present invention provides a convenient, simple means for unloading differentially separated materials. In addition, unlike conventional straight-wall tubes, if the centrifuge tube of present invention is dropped or accidentally inverted, the contents will not readily mix due to the presence of the constriction member. Moreover, once separation has taken place, the solution present above the constriction member can be mixed in the tube, without disturbing (or fear of contamination by) the contents of the tube below the constriction member.

In an alternative preferred embodiment, tube 10 may be provided with insert or shield 30, as shown in FIGS. 2 and 2B. Shield 30 is provided above constriction member 12 to facilitate layering of the sample onto the gradient solution. Shield 30 may take the form of a roughly concentric insert placed in the upper portion of the tube and extending at least partially around the tube. In use, the operator pipettes material between shield 30 and the tube wall. The shield directs the material along the side of the tube to the top of the density gradient solution, while minimizing disturbance of the solution. As shown in FIG. 2B, tube 10 is a clear plastic or glass, with constriction member 12 formed as a separate silicone insert. Shield 30 can be held in the upper portion of the tube, for example, by interference fit with spacers 31 biasing against the tube wall. Alternatively, shield 30 could be formed as a part of the tube.

The separation of materials may be further enhanced by the addition of valve 40 to the constriction member, as shown in FIG. 3. The valve 40 is located across opening 14. Valve 40 may be a one-way valve, or a valve that only opens upon application of a threshold centrifugal force. The valve can be formed by providing flaps of a softer material over the opening. In a preferred embodiment, the force required to open valve 40 would be about 850 times the normal force of gravity. Valve 40 thus allows heavy cells to pass through during initial centrifugation, and then keeps those cells in place, allowing for further processing of the lighter cells of interest located above the valve (such as washing or mixing of the cells). In this way complete and final manipulation of the cells can be performed in a single sterile container.

The shape of opening 14 is not limited to a circular shape, though in general, a funnel-shaped restriction forming a roughly circular shape 14A will be preferred. As shown in FIGS. 4A–4D, the opening may also be oval 14B, rectangular 14C, star-shaped 14D, or any other shape that would create a restriction.

FIGS. 5A–5F are illustrations of alternative shapes and designs for the tube and constriction member according to the invention. FIG. 5A shows alternative tube 42 having a separate bottom compartment 44 for receiving the pellet to provide optimal collection of cells. Constriction member 12 is as previously described; it is funnel shaped on its upper surface and formed from a separate insert of plastic or, preferably, silicone. FIG. 5B shows a tube 46 with a pointed bottom wall. Tube 46 with the pointed bottom wall also enhances cell collection by allowing the heavier cells to form a better pellet, which may be desired if the cells are to be collected. Constriction member 48 is again an insert, but with a flat upper surface and wider opening. FIG. 5C illustrates alternative tube 50 with an integrally molded constriction member 52. FIG. 5D shows an alternative constriction member 54 that facilitate movement within tube 55 to adjust the relative volumes of the upper and lower portions. For this reason constriction member 54 has annular extendings contact points 56. The constriction member will only contact the tube at these points, which create a fluid tight seal, but allow for easier adjustability. Tube 55 also has a flat bottom. FIG. 5E illustrates a further alternative embodiment of the present invention, wherein tube 60 includes cell trapping material 62, such as a sponge or gel. Material 62 may contain compounds that specifically bind certain cell types or toxins that kill specific cell types. Material 62 also may be made of a magnetic material if desired. Tube 64, shown in FIG. 5F, illustrates a further example of an integrally formed constriction member 66 in a tube with a flat bottom wall 68. Construction member 66 is located such that lower portion 26 has a smaller relative volume.

FIGS. 6A and 6B illustrate further alternative embodiments of the tube according to the invention. In each, two constriction members are provided. Second constriction member 12A is located above first constriction member 12B to create more compartments to allow separation of cells of differing densities. In FIG. 6A, the constriction members are shown as separate inserts, whereas they are integrally formed with the tube in FIG. 6B. Additional constriction members could also be added if a sample of several different densities is to be separated.

It will be applied by persons of ordinary skill in the art that the embodiments of FIGS. 2–6 are illustrated herein without density gradient solution for the sake of clarity only. Preferably, each embodiment would contain density gradient solution as described herein in connection with the embodiment of FIG. 1.

In a preferred embodiment, the cell-trap tube may be used in the form of a centifuge syringe, which is a completely enclosed system to ensure sterility.

One embodiment of centrifuge syringe 110 according to the invention is illustrated in FIG. 7. The centrifuge syringe includes a specimen container 114 with a central orifice surrounded by fitting 112 adapted for receiving a needle 113, a handle 116 and a plunger 118. Fitting 112 may be any type of locking tip adapted to hold a needle, for example, a Luer-Lock™ syringe tip. Alternatively, fitting 112 may be a sterile septum adapted for connection with sterile fluid bags and tubes, for example a SAFSITE™ small wire extension set with reflux valve and Spin-Lock™ adaptor available from Burron Medical Inc., Bethlehem, Pa.

Handle 116 further preferably comprises knob 122 and a removable connection 124 to plunger 118. As shown in FIGS. 7–10, plunger 118 is single piece, machined or molded from a plastic material. Known medical grade plastic materials may be used. The plunger preferably has a funnel-shaped bottom wall 126 that is removably connected to the handle at connection 124. Side wall 127 preferably closely matches the container wall to permit sliding movement but provide an essentially fluid-tight barrier therearound. A top wall is formed by constriction member 128, which defines central opening 129. Alternatively, the outer diameter of side wall 127 may be slightly undersized to facilitate sliding and an o-ring seal provided between side wall 127 and container 114. Removable connection 124 may take the form of, for example, a screw fitting or a snap-fit. Preferably, connection 124 also provides for reattachment of handle 116. If reattachment is not desired, connector 124 may be designed such that handle 116 can be broken off. A suitable connection can be selected by those of ordinary skill in the art.

The plunger 118 is filled with a density gradient material 120 before the introduction of a specimen. Preferably, the density gradient material is filled to a level above the constriction member, or at least above the top of opening 129. For example, when using a standard 50 ml syringe, having an inner diameter of about 2.8 cm, the gradient material is preferably filled to a level about 1 mm or more above constriction member 128. This fill level will help to prevent the formation of an interface portion, as explained below, under constriction member 128.

Referring to FIG. 8, the introduction of the specimen into centrifuge syringe 110 is illustrated. Specimen 130 is drawn into the syringe through needle 113 secured to fitting 112, aided by the vacuum created by handle 116 and plunger 118 as the handle is pulled out of container 114, drawing the plunger away from fitting 112. The handle should be pulled with sufficiently low force and velocity to avoid mixing of the specimen with the density gradient material onto which the sample is layered. Preferably, when the handle is pulled at an appropriate force, the sample will form a stream which adheres to the side of the container as it is drawn in, as shown in FIG. 8. This will reduce unwanted mixing. Mixing of the two materials is also minimized by the fact that the density of the specimen is significantly lower than the density of the density gradient material. After specimen 130 is drawn into container 14, the container is maintained in an upright position and the sample lies on top of density gradient material 120.

Using needle 113, a sample such as peripheral blood may be drawn directly from a patient for analysis. The present invention thus ensures sterility of such a sample by completely eliminating direct handling of the sample prior to introduction into the centrifugation container. Alternatively, using a sterile septum, blood previously collected by known techniques and stored, for example in a sterile bag, may be drawn into the centrifugation container through sterile tubing or other known sterile connection means. The present invention thus ensures a sterile transfer of sample material on a larger scale in a completely closed system, again without direct handling of sample material.

Once the specimen has been completely drawn into the container 14, and the handle 116 has been pulled so that the removable connection 124 is located at the central orifice of the specimen container 14, the handle 116 can be removed for the centrifugation step.

FIG. 9 illustrates the centrifugation syringe after the centrifugation step has been performed. As shown, the handle 16 has been detached from the plunger 118, which is located at the bottom end of the container 114. Centrifugation of container 114 results in a pellet 142 being formed from the heavier portions of the specimen at the bottom of the plunger 118. Density gradient material 120 is located above pellet 142. An interface portion 134, which contains the cells of interest, is formed between specimen diluent 143 and density gradient material 120, and above constriction member 128.

Interface portion 134 may be removed from the centrifuge syringe 10 by inverting the centrifuge syringe and ejecting it off as indicated by arrow 147 in FIG. 10. Further removal of density gradient material 120 and the pellet 142 can be facilitated by reattaching handle 116 to plunger 118. The handle then can be pushed into the container to aid the removal of the material if necessary.

5.4. DENSITY ADJUSTED CELL SEPARATION

Density gradient centrifugation is a method of separating cells based on the different densities of cell types in a mixture. The method is often used in a single step to separate cells into two compartments which contain cells that are either lighter or heavier than a specific density of the gradient material used. However, due to the imprecision of the procedure, the use of a single density gradient usually does not allow the cells of interest to be enriched to a significant level of purity, especially if the cells are present in a low number among many undesired cell populations. Thus, density gradient centrifugation is most often carried out through repetitive steps based on a series of different density gradients or in combination with affinity separation, cell panning, cell sorting, and the like. Alternatively, density gradient centrifugation may be performed using multiple layers of the different gradient densities. This method allows cells of different densities to form zones or bands at their corresponding densities after centrifugation. The cells in the different zones are then collected by placing a pipette at the appropriate location. Such a method is difficult to carry out in a routine manner in a clinical setting because it requires skilled personnel for the preparation of the gradient, and there is often mixing between the different layers of the density solution before and/or after centrifugation that potentially disrupts cell separation. Most importantly, the above-described procedures require multiple steps that unavoidably cause substantial cell loss, thus they are not amenable for the separation of cells present in a low number within a mixture in a routine manner.

Figure 11A:
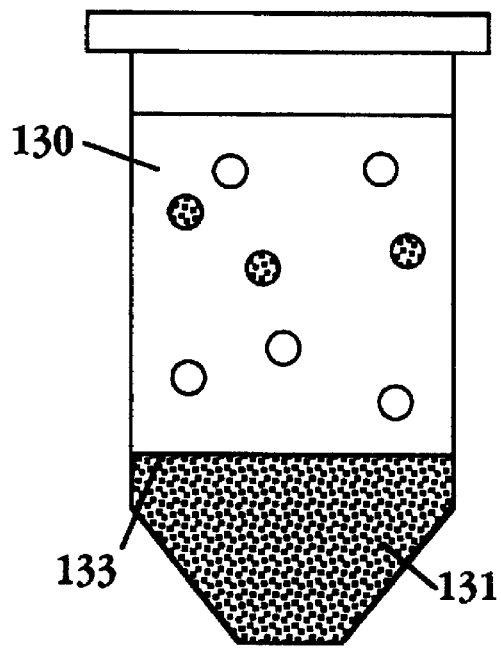
Figure 11B:
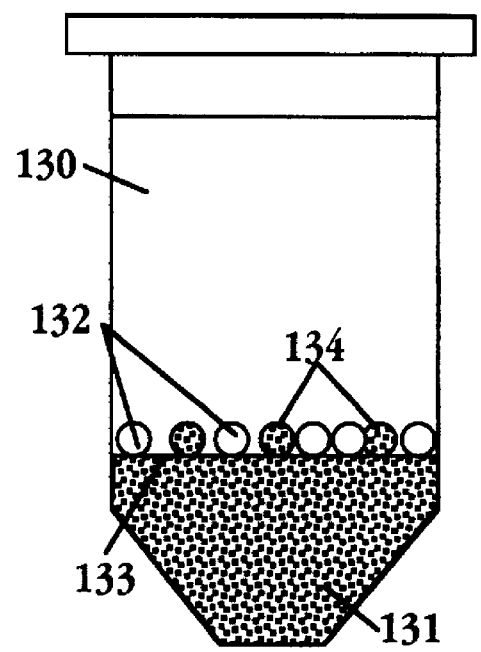
Figure 11C:
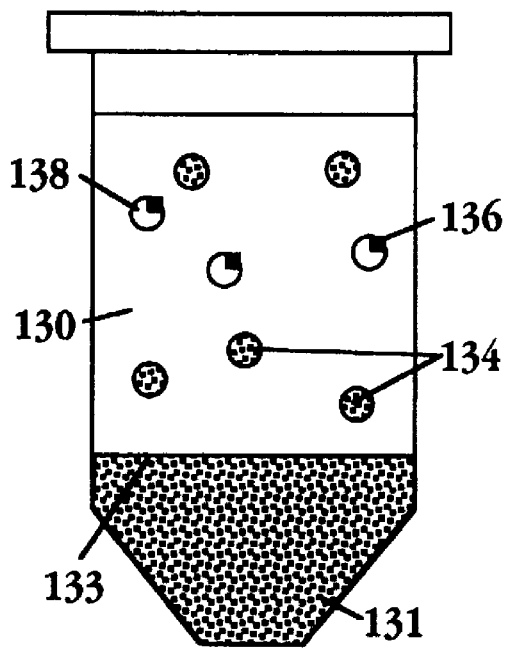
Figure 11D:
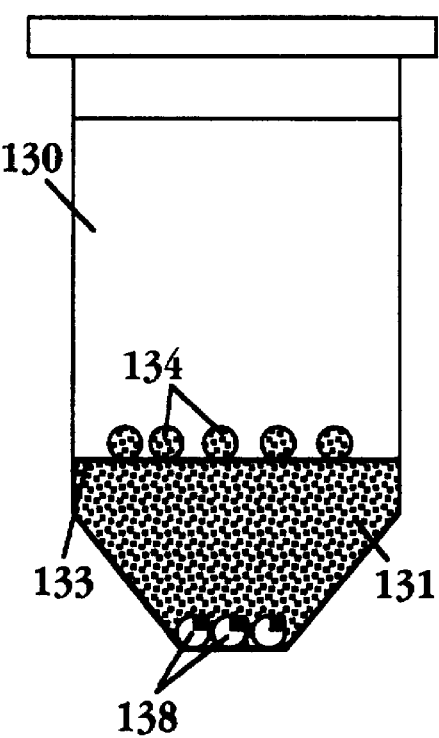

The present invention circumvents these problems by combining density gradient centrifugation and affinity cell separation into a single method referred to as density adjusted cell sorting. This method modifies the conventional positive and negative selection by solid phase binding methods, and combines it with the specific density for a given cell type. FIGS. 11(A–D) demonstrate the use of density adjusted cell sorting (FIGS. 11C and 11D) as compared to conventional density gradient centrifugation (FIGS. 11A and 11B). While the conventional methods are able to concentrate many irrelevant cell types to form a pellet, there are still a large number of undesired cell types trapped at the interface with the cells of interest (open circles, FIG. 11B). However, density adjusted cell sorting provides for the use of affinity modified carrier particles wherein cell type-specific binding agents, e.g. for example, peptides; polypeptides; serological factors, e.g. antibodies or antigens, growth factors; lectins, e.g. Helix pomatia Lectin (available from Pharmacia Fine Chemicals), or other affinity molecules having specificity for either the desired cell populations or the undesired cell populations, are bound either directly or indirectly to a carrier particle. The affinity modified carrier particles are incubated with the cell mixture prior to centrifugation, such that density-adjusted cells are separated from the bodily fluid or tissue sample during centrifugation (as illustrated by solid squares and open circles, FIGS. 11C and 11D). For cells which are normally lighter than the gradient density, a heavier density may be imparted to them by use of heavy carrier particles, e.g. silica particles, which may be rendered cell type-specific by the direct or indirect binding of cell type-specific binding agents. Alternatively, for cells which are heavier than the gradient density, a lighter density may be imparted to them by use of lighter carrier particles, e.g. highly porous silica particles which are rendered cell type-specific by the direct or indirect binding of cell type-specific binding agents. When density adjusted cell sorting is applied to a cell or tissue sample which is overlaid onto a customized density gradient contained within a cell-trap centrifugation tube, a single centrifugation step allows for substantial enrichment of a cell type of interest from the sample. Density adjusted cell sorting may be applied in a negative affinity manner, i.e., to purge undesired cells, e.g. tumor cells, from a sample by using a modified carrier particle having specificity for the undesired cell population; alternatively, density adjusted cell sorting may applied in a positive affinity manner, i.e., to collect desired cells from a sample by using a modified carrier particle having specificity for the desired cell population. The beads may be removed from desired cells by enzymatic or chemical cleavage. For example, papain may be used to cleave a desired cell from immunoglobulins. After the first round of centrifugation and collection of enriched cells, a second round of centrifugation including density adjusted cell sorting may be performed to further enrich for the desired cell population. Example 6, infra, shows that complete blood from pregnant females could be directly incubated with carrier particle-coated-anti-CD45 antibodies which reacted with most leukocytes. The vast majority of human cells were rendered heavier that the density material upon centrifugation thereby enriching for the desired fetal cells.

A number of commercially available carrier particles may be used in the present invention and include, for example, organic polymers, e.g. polyethylene; polypropylene; polyvinyl compounds e.g. polyvinylchloride, polyacrylonitrile, polyacrylate, polymethacrylate, polycarbonate and copolymers thereof; polystyrene latex; nylon; polyterephthlate; and the like, or inorganic polymers, e.g. glass or silica particles; cellulose, Dextrans, polysaccharides, e.g. agarose, cellulose, Sepharose, Sephadex, etc., or combinations thereof. The carrier particles may be from naturally occurring polymers, modified naturally occurring polymers and synthetic addition and condensation polymers. A preferred carrier particle of the present invention is a silica particle between 0.1–5.0 microns coupled to an aminopropyl group and having a density of greater than 1.08 gr/ml. U.S. Pat. Nos. 4,927,750 and 4,927,749, issued May 22, 1990, describe examples of modified silanes which may be used in the present invention as carrier particles. Various carrier particles are commercially available from, for example, Bangs Laboratories, Inc., Carmel, Ind., Pharmacia, Sigma Chemical Company, Bio-Rad, AMAC, Inc., etc.

A preferred heavy carrier particle of the present invention is a silica bead having a density greater than the density of the density gradient material selected according to methods described infra and a particle size of 0.1 micron to 5.0 micron such that the carrier particles will be pelleted upon centrifugation, as well as one having the capability of binding, either directly or indirectly to cell type-specific binding agents. The carrier particles may additionally be derivatized to substances, e.g. lectins, wheat germ or soy agglutinins, or sugars, to impart an even greater density. A preferred lighter carrier particle of the present invention is one having a density less than 1.0 and a particle size of 0.1 to 5.0 microns, such that the particles will float above the density gradient upon centrifugation as well as one having the capability of binding, either directly or indirectly to cell type-specific binding agents. Such low density carrier particles can be obtained from 3M, St. Paul Minn. catalog no. H50/1000, termed "Scotchlite microbeads". In the cell separation method of the present invention, the desired or undesired cell populations may be enriched through use of affinity modified carrier particles imparting either heavier or lighter densities.

The surface of polystyrene latex particles (available from Sigma Chemical Company), is hydrophobic and certain types of serological factors, e.g. antibodies, may be adsorbed on the surface under carefully controlled conditions. Such hydrophobic particles may stick non-specifically to many surfaces and molecules, therefore precaution must be taken to adsorb the serological factor to the polystyrene carrier in excess serological factor to avoid any non-specific binding of the polystyrene particle. Alternatively, the addition of methacrylic acid residues to the polystyrene latex particles will impart a negative charge onto the particles which may prevent non-specific binding to cell surfaces. Polystyrene beads may require modification to impart a heavier density, e.g. through addition of metal groups, in order to affect pelleting upon centrifugation.

Polyacrylamide carrier particles provide less non-specific binding than polystyrene latex beads. Bio-Rad provides derivatized polyacrylamide beads coupled to either primary amino functional groups, Affi-Gel 701 beads, or carboxyl functional groups, Affi-Gel 702 beads or Immunobead Reagent which may be used to bind serological factors to the derivatized polyacrylamide beads.

The preparation of small, stable, spherical particles which are bio-compatible, i.e., do not interact non-specifically with cells or other biological components and which contain functional groups to which specific proteins and other biochemical molecules can be covalently bonded is disclosed in U.S. Pat. No. 3,957,741, issued May 19, 1976. The hydroxyl or amino groups can be activated by cyanogen bromide for covalent bonding of protein and other chemicals containing amino groups to the polystyrene latex.

U.S. Pat. No. 4,035,316, issued Jul. 12, 1977, describes the method for making cell specific, variable density, polymeric microspheres derivatized with amine-, hydroxyl- and/or carboxyl-functional groups and having a density of at least 1.30 gr/ml preferably above 1.40 gr/ml or a density below 1.15 gr/ml and preferably below 1.08 gr/ml.

A process for forming highly uniform silica spheres is described in U.S. Pat No. 4,983,369, issued Jan. 8, 1991.

Also included within the scope of the present invention are carrier particles or carrier particles to which are attached a magnetic substance allowing for enhanced separation of cells through use of a magnetic field. U.S. Pat. No. 4,777, 145, issued Oct. 11, 1988 describes an immunological assay method using magnetic particles. AMAC, Inc., subsidiary of IMMUNOTECH, S.A. (France) provides magnetic microspheres coated with monoclonal antibody, e.g. anti-CD4, anti-CD8, anti-CD19, anti-45, etc.

5.4.1. CELL TYPE-SPECIFIC BINDING AGENTS

The cell separation methods of the present invention provide for the use of cell type-specific binding agents having specificity for either the desired or undesired cell populations which may be bound either directly or indirectly to a carrier particle. As defined herein, "cell type-specific binding agents" are those agents, for example, antibodies or antigens; peptides or polypeptides; growth factors or cytokines; lectins and agglutinins which either bind specifically to a single cell type or bind specifically to a defined group of cell types and not others. For example, a carrier particle coated with anti-CD-45 antibodies will specifically bind to most maternal leukocytes in maternal whole blood, but not to fetal nucleated red blood cells allowing for the enrichment or separation of fetal cells from maternal whole blood. In another example, a carrier particle coated with wheat germ agglutinin will bind to lymphocytes and less to granulocytes allowing for the positive enrichment of lymphocytes and negative enrichment of granulocytes.

The variety of commercially available cell type-specific binding agents may be used in the present invention, including, but not limited to, antibodies, antigens, polypeptides, peptides, growth factors, membrane bound receptors, small organic molecules, lectins, and agglutinins.

A variety of antibodies known to those of skill in the art, commercially available or available through cell culture depositories, e.g. the ATCC, Rockville, Md. or the NRLL, Peoria, Ill., may be used in the present invention as cell type-specific binding agents depending upon the cell type desired to be isolated or enriched and include, but are not limited to, antibodies specific to hematopoietic and lymphoid antigens such as, anti-CD2, anti-CD2R, anti-CD3, anti-CD4, anti-CD5 and anti-CD8 specific for T cells; anti-CD6 specific for T-cell subset and B-cell subset; anti-CD7 specific for major T-cell subset; anti-CD12, anti-CD19 and anti-CD20, anti-CD72, anti-CDw78, specific for B cells; anti-CD13 and anti-CD14 specific for monocytes; anti-CD16 and anti-CD56 specific for natural killer cells; anti-CD41 for platelets; anti-CD1a, CD1b and CD1c specific for cortical thymocytes and Langerhans cells; anti-CD9 specific for pre-B-cells, monocytes & platelets; anti-CD10 specific for lymphoid progenitor cells, C-All and granuloytes; anti-CD11a specific for leucocytes; anti-CD11b specific for granulocytes, monocytes and natural killer cells; anti-CD11c specific for monocytes, granulocytes, natural killer cells and hairy cell leukaemia; anti-CD15 specific for granulocytes; anti-CDw17 specific for granulocytes, monocytes and platelets; anti-CD18 specific for leucocytes; anti-CD21 specific for mature B-cells; anti-CD22 specific for B-cells cytoplasm and mature B-cells; anti-CD23 specific for activated B-cells; anti-CD24 specific for B-cells and granulocytes; anti-CD25 and anti-CD26 specific for activated T- and B-cells and activated macrophages; anti-CD27 and anti-CD28 specific for major T-cell subset; anti-CD30 specific for activated T- and B-cells and Sternberg Reed cells; anti-CD31 specific for platelets, monocytes/macrophages, granulocytes and B-cells; anti-CDw32 specific for macrophages, granulocytes, B-cells and eosinophils; anti-CD33 specific for monocytes, myeloid progenitor cells and myeloid leukaemias; anti-CD34 specific for haematopoietic precursor cells; anti-CD35 specific for granulocytes, monocytes, B-cells, some NK cells, and erythrocytes; anti-CD36 specific for monocytes/macrophages and platelets; anti-CD37 specific for mature B-cells; anti-CD38 specific for plasma cells, thymocytes and activated T-cells; anti-CD39 specific for mature B-cells; anti-CD40 specific for B-cells and carcinoma; anti-CD42 and 42b specific for platelets and megakaryocytes; anti-CD43 specific for leucocytes except circulating B-cells; anti-CD44 specific for leucocytes and Red cells; anti-CD45 specific for leucocytes; anti-CD45RO specific for T-cells, B-cells subset, monocytes and macrophages; anti-CD45RA specific for B-cells, monocytes and T-cell subset; anti-CD45RB specific for B-cells, T-cells subset, monocytes macrophages and granulocytes; anti-CD46, CD55, CD58 and CD59 specific for haematopoietic and non-haematopoietic cells; anti-CD47 specific for all cell types; anti-CD48 specific for leucocytes and neutrophils; anti-CDw49b specific for platelets, activated & long-term cultivated T-cells; anti-CDw49d specific for monocytes, T-cells & B-cells; anti-CDw49f specific for platelets and megakaryocytes; anti-CDw50 & CDw52 specific for leucocytes; anti-CD51 specific for platelets; anti-CD53 specific for leucocytes including normal and neoplastic plasma cells; anti-CD54 specific for endothelial cells; anti-CDw60 specific for T-cells subset and platelets; anti-CD61 specific for platelets & megakaryocytes; anti-CD62 specific for activated platelets; anti-CD63 specific for activated platelets, monocytes/macrophages; anti-CD64 specific for monocytes (upregulated interferon γ); anti-CDw65 specific for granulocytes and heterogenons reactivity with monocytes; anti-CD66 & 67 specific for granulocytes; anti-CD68 specific for monocytes and macrophages; anti-CD69 specific for activated B- and T-cells, activated macrophages, and natural killer cells; anti-CDw70 specific for activated T- and B-cells, Sternberg-Reed cells, and anaplastic large cell lymphoma; anti-CD71 specific for activated T- and B-cells, macrophages, proliferating cells; anti-CD73 specific for B-cell subset and T-cell subset; anti-CD74 specific for B-cells and monocytes/macrophages; anti-CDw75 specific for mature B-cells; anti-CD76 specific for mature B-cells and T-cell subset; anti-CD77 specific for follicular center B-cells; antibodies to cytokines and growth factors (e.g. IL1–IL13, EGF, IGF I and II, TGF-α and β, TNF-α and β, FGF, NGF, CIF, IFN-α and β, CSF's); viral antigens (e.g. Hepatitis B virus envelope proteins or HIV envelope proteins), hormones, cellular or tumor associated antigens or markers, adhesion molecules, hemostasis molecules, and endothelial cells.

Various procedures known in the art may be used for the production of antibodies to a particular cell type. Such antibodies include but are not limited to polyclonal, monoclonal, chimeric, single chain, Fab fragments and fragments produced by a Fab expression library and phage display expression library. For the production of antibodies, various host animals may be immunized by injection with an antigen including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, BCG (bacilli Calmette-Guerin) and *Corynebacterium parvum*.

Monoclonal antibodies to an antigen of interest may be prepared by using any technique which provides for the production of antibody molecules by continuous cell lines in culture. These include but are not limited to the hybridoma technique originally described by Koehler and Milstein, (*Nature*, 1975, 256:495–497), the human B-cell hybridoma technique (Kosbor et al., 1983, *Immunology Today* 4:72; Cote et al., 1983, *Proc. Natl. Acad. Sci.* 80:2026–2030) and the EBV-hybridoma technique (Cole et al., 1985, *Monoclonal Antibodies and Cancer Therapy*, Alan R. Liss, Inc., pp. 77–96). In addition, techniques developed for the production of "chimeric antibodies" (Morrison et al., 1984, *Proc. Natl. Acad. Sci.* 81:6851–6855; Neuberger et al., 1984, *Nature*, 312:604–608; Takeda et al., 1985, *Nature* 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce specific single chain antibodies.

Antibody fragments which contain specific binding sites may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, *Science* 246:1275–1281) to allow rapid and easy identification of monoclonal Fab fragments with the desired specificity the antigen of interest.

The cell separation method of the present invention may be used with cell type-specific binding agents having specificity for soluble or cytosolic polypeptides or growth factors as long as the soluble polypeptides or growth factors are expressed on the cell surface prior to being secreted.

A variety of agglutinins are commercially available that may be used in the present invention including, but not limited to, wheat germ agglutinin, peanut agglutinin, soy bean agglutinin, phytohaemagglutinin, and leucoagglutinin. Such agglutinins are commercially available, for example, from Pharmacia.

5.4.2. COUPLING OF CELL TYPE-SPECIFIC BINDING AGENTS TO CARRIER PARTICLE

Immobilization of the cell type-specific binding agent to the carrier particles can be achieved by a variety of techniques known to those of skill in the art. Such techniques are described in, for example Bangs (*The Latex Course* (1992), available from Bangs Laboratories, Inc. Carmel, Ind.); Yoshioka et al., 1991, *Journal of Chromatography* 566:361–368; Pope et al., 1993, *Bioconjugate Chem.* 4:166–171); Harlow and Lane, 1988, *Antibodies: A Laboratory Manual*, Colorado Spring Harbor Laboratory; *Avidin-Biotin Chemistry: A Handbook*, 1992, ed. Savage et al., pub. PIERCE; Hermanson et al., *Immobilized Affinity Ligand Techniques*, 1992, pub. Academic Press, Inc.

Binding techniques include, for example, simple physical absorption or adsorption where the cell type-specific binding agent is bound directly to the carrier protein without the use of functional groups; complex adsorption where a second binding agent, e.g. BSA, is co-adsorbed to the carrier particle and forms the basis for binding functional groups; and covalent bonding of the binding agent to the carrier particle. The biotin-strepavidin affinity system may also be used in the present invention to bind cell type-specific binding agents to the carrier particles. Various particle surface chemical reactions for covalent coupling are known to those of skill in the art and include, but not limited to, carboxylic acid, primary or aliphatic amine, aromatic amine or aniline, chloromethyl (vinyl benzyl chloride), amide, aldehyde, hydroxyl, thio, hydrazide, epoxy, sulfate and sulfonate. Other coupling chemical reactions are described in Bangs, Uniform Latex Particles (1984).

In the present invention, it is preferred that the direct or indirect binding of the cell type-specific binding agent to the carrier particle be performed in excess binding agent to allow for maximum coverage of the surface of the carrier particle, thereby reducing the potential for non-specific binding and bead clumping. Carrier particles may also be subjected to blocking agents, e.g. casein, gelatin and Tween to fill any unoccupied sites on the carrier particle in order to reduce non-specific binding.

In one illustrative example of a coupling reaction, carboxyl groups on the carrier particle surface can be made reactive with the available amino groups on the cell type-specific binding agent. Other means of binding cell type-specific binding agent to particle surfaces include employing activated carboxylic acids, carbodiimides, i.e., (1-ethyl-3-(3-dimethylaminopropyl)carbodiimide or EDAC, imido esters, active alkyl halides, etc., to form amido, amidine or amino linkages.

A preferred carrier particle of the present invention is an aminopropyl silica particle wherein the amino groups have been coupled to the silica particle through a glutaraldehyde linkage, see example 9.

5.5. PRACTICE OF THE INVENTION

The present invention provides methods for one of a skill in the art to isolate or enrich for a desired cell type from an in vivo or in vitro mixture. According to the teachings provided herein, the specific density of the desired cell type is determined by subjecting a solution or mixture containing the desired cell to discontinuous gradient centrifugation. As described in Section 5.2, the discontinuous gradient centrifugation is carried out on sequentially narrower ranges of specific gravity of gradient material, with intervals between adjacent gradient solutions ranging from 0.01 gr/ml to 0.005 gr/ml to 0.0005 gr/ml. The invention is based, in part, on the accuracy of the density gradients, i.e., the density gradients must be prepared such that their densities are accurate to within at least ±0.0005 gr/ml of the desired density gradient, preferrably within ±0.0002 gr/ml of the desired density gradient, and a defined osmolality.

After the specific density of a desired cell type is determined, the desired cell can be isolated or enriched by subjecting a solution or mixture containing the desired cell type to single step gradient centrifugation on a gradient material having a specific gravity within ±0.0005 gr/ml of the specific gravity of the cell. More preferably, the specific gravity of the gradient material is within ±0.0002 gr/ml of the specific gravity of the cell. Such centrifugation is preferably carried out in a cell-trap centrifugation tube, as described in Section 5.3. Following centrifugation, the desired cell will be found at the interface between the gradient material and the cell sample solution. Material at the interface can be collected, then centrifuged to concentrate it, if desired. Alternatively, when it is preferable to retain the desired cell material in a closed system, the centrifugation can be carried out in a centrifugation syringe having a cell-trap configuration, such as described in Section 5.3.

If desired, improved purity of the desired cell type can be effected by adding to the above procedure a density-adjusted cell sorting procedure, as described in Section 5.4. In this procedure, prior to centrifugation, the cell sample containing the desired cell is exposed to carrier particles having bound thereto cell type-specific binding agents, e.g. antibodies which do not bind the cell of interest but which do bind to non-desirable cells (negative affinity) or alternatively, antibodies which bind to the desired cells and not to non-desirable cells (positive affinity). The carrier particles may have a density that is heavier or lighter than that of the density gradient material in the tube, and consequently the desired cells may be drawn into the pellet formed during centrifugation, or left in the supernatant depending upon the binding affinity of the cell type-specific binding agent.

For therapeutic applications, it is preferred that the desired cell population remain in the interface between the gradient material and the cell sample solution, i.e., through negative affinity selection. Alternatively, if the desired cells are found attached to beads in the pellet, the desired cells may be cleaved enzymatically or chemically from the beads by methods known to those of skill in the art, including the use of proteolytic enzymes, e.g. papain.

The cells isolated or enriched by the cell separation methods described herein may be used for a variety of diagnostic and therapeutic uses. The isolated or enriched cells may be cultured under sterile conditions and subjected to cytogenetic analysis, e.g. the detection of chromosomal abnormalities and gender determination. The isolated or enriched cells may be reacted with molecular probes for more sensitive detection using PCR and FISH. The isolated or enriched cells may also be used therapeutically, for example, for allogeneic and autologous transplantation.

6. EXAMPLE: ENRICHMENT OF FETAL NUCLEATED RED BLOOD CELLS FROM MATERNAL BLOOD

6.1. MATERIALS AND METHODS

6.1.1. PREPARATION OF DENSITY GRADIENTS

"PERCOLL" solution was purchased from Pharmacia Biotech (Uppsala, Sweden) and stored at 4° C. according to the recommendation of the vendor. A stock solution was prepared by mixing 12 parts of "PERCOLL" with 1 part of 10×calcium and magnesium-free phosphate buffered saline (PBS). The pH of the solution was adjusted to 7.4 and the osmolality to 280±10 mOsm/Kg $H_2O$. For use in separating fetal nucleated red blood cells in a blood sample, the stock solution was further diluted with calcium and magnesium-free PBS to a density of 1.0720±0.0005 gr/ml and used at room temperature. It was important to adjust the density of the gradient to an accuracy within ±0.0005 gr/ml, preferably within ±0.0002 gr/ml of 1.0720 gr/ml in order to ensure reproducibility and accuracy of cell separation. This was done by a high precision digital density meter such as DMA 48 (Anton PAAR U.S.A., Ashland, Va.). All procedures were performed under sterile conditions and at room temperature.

6.1.2. COLLECTION AND PROCESSING OF BLOOD SAMPLES

Peripheral blood was collected from pregnant females in anti-coagulant-containing tubes. The collection was performed before week 20 of pregnancy because the number of fetal cells circulating in maternal blood generally began to decline after week 17 of pregnancy. In fact, the preferred end point for blood collection was before week 17 of pregnancy with week 13 being the optimal time point for highest numbers of fetal cells in maternal circulation. After collection, the blood samples were processed within 48 hours, since there was a prominent reduction in accuracy of cell separation on the density material with samples used 48 hours after collection.

6.1.3. DENSITY GRADIENT CENTRIFUGATION OF PERIPHERAL BLOOD

Complete blood samples were layered on a "PERCOLL" gradient previously adjusted to a density of 1.0720±0.0002 gr/ml, an osmolality of 280 mOsm/Kg $H_2O$, and a pH of 7.4 in a 50 ml conical cell-trap tube. The tube contained a constriction in a location so that approximately 15 ml of "PERCOLL" was in the lower compartment and 5 ml of "PERCOLL" was above the constriction. It was critical to completely fill the volume under the constriction with "PERCOLL" to prevent the formation of air bubbles. Generally, 20 ml of blood samples were layered on top of this gradient. The tube was centrifuged at 850×g for 30 minutes at room temperature. The cells lodged at the interface of the gradient; i.e., on top of "PERCOLL," were collected by pouring the entire content of the upper compartment of the tube into another 50 ml tube. The cell pellet in the region below the constriction were prevented from pouring off when the tube was inverted. After centrifugation at 650×g for 10 minutes at room temperature, the fluid on top of the pellet was removed with a pipette, and the cells in the pellet resuspended in PBS. Since this low speed centrifugation step was primarily used to concentrate the cells of interest into a pellet, while removing cell debris and platelets in the upper region, a cell-trap could also be used to facilitate this step. In this alternative embodiment, a modified 50 ml cell-trap tube was used in which the constriction was placed near the bottom of the tube so that a small volume of about 0.5 ml was below it. This design would protect the pellet and reduce cell loss during removal of the fluid above the pellet after centrifugation. This specific feature would also allow the method of the invention to be used in an automated fashion without the need for a subsequent cell sorting step, which was performed to reduce contaminating cells, particularly platelets.

In order to compare the cell separation method described in the preceding paragraph with conventional methods, the following procedure was also carried out as a control. This procedure was similar to previously published methods known in the art (Bianchi et al., 1990, Proc. Natl. Acad. Sci. U.S.A. 87:3279). The blood sample was collected as described above and diluted 1:4 in PBS. The diluted blood was layered on "FICOLL-HYPAQUE" (Pharmacia) in 4 different 15 ml tubes. The density of the stock "FICOLL" solution was at 1.077±0.001 gr/ml and the osmolality at 320 mOsm/kg $H_2O$ as published by Pharmacia. The tubes were centrifuged at 850×g for 20 minutes at room temperature. The cells at the interface above the "FICOLL" were collected with a pipette and transferred to two 15 ml tubes. The tubes were filled to the top with PBS and spun at 650×g for 10 minutes at room temperature. The fluid on top of the pellet was aspirated with a pipette, and the pellet resuspended in PBS. In addition, experiments were also performed using cell-trap tubes with "FICOLL" solution in an effort to increase cell yield.

6.1.4. AFFINITY SEPARATION BY A MAGNETIC FIELD

The fetal nucleated red blood cells resuspended in PBS after density gradient centrifugation described in Section 6.1.3 were further enriched through removal of $CD45^+$ leukocytes by incubating the cells with an anti-CD45 monoclonal antibody (clone ALB-12) (Biodesign International, Kennebunk, Me.) for 30 minutes at 4° C. The unbound antibodies were removed by washing the cells in PBS. A goat-anti-mouse antibody conjugated to magnetic particles (Immunocon) was added to the cells for 30 minutes at 4° C. The cells were washed in PBS and exposed to a magnetic field which attracted the magnetic particle-coated $CD45^+$ leukocytes, while the fetal nucleated erythroid and trophoblast cells remained in solution. The fetal cells were collected with a pipette and washed once in PBS. The cells were then tested by antibody staining and flow cytometric analysis to determine the number of nucleated red blood cells.

6.1.5. DENSITY ADJUSTED CELL SORTING

Complete blood collected from pregnant females was incubated with 1.4μ aminopropyl glass beads (Bangs Laboratories Inc., Carmel, Ind.) that were glutaraldehyde coated with an anti-CD45 antibody (ALB-12) for 45 minutes at room temperature. The entire blood cell mixture was layered on "PERCOLL" (1.0720±0.0002 gr/ml, 280 mOsm/Kg $H_2O$, pH 7.4) in a 50 ml cell-trap tube. The tube contained about 15 ml of "PERCOLL" below the constriction and about 5 ml above it. It was critical to completely fill the volume under the constriction with "PERCOLL" to prevent the formation of air bubbles. The tube was centrifuged at 850×g for 30 minutes at room temperature. The leukocyte-depleted cell population was collected from the interface above the "PERCOLL" by pouring off the entire upper region of the tube into a 50 ml tube. The cells were spun at 650×g for 10 minutes at room temperature, and the fluid on top of the pellet removed with a pipette. The cells in the pellet were resuspended in PBS. Alternatively, the second centrifugation step could be carried out in a modified cell-trap tube as described in Section 6.1.3, supra. Additionally, a second density adjusted cell sorting could also be performed using antibodies such as anti-CD41 to specifically remove platelets.

6.1.6. ANTIBODY STAINING AND FLOW CYTOMETRIC ANALYSIS

The leukocyte-depleted cell population in PBS were treated with the DNA dye LDS 751 (Exciton, Inc., Dayton, Ohio) and erythroid lineage specific FITC-conjugated monoclonal antibodies such as anti-glycophorin A and anti-CD71 (Becton Dickinson, Inc., San Jose, Calif.). The LDS 751 dye distinguished between nucleated and a nucleated cell. One million cells were incubated with 10 μl antibodies for 30 minutes at 4° C. in the presence of 5% rabbit serum and LDS 751. The cells were washed twice with PBS and fixed in 1% paraformaldehyde. The antibody-bound cells were analyzed by flow cytometry for which statistical analysis was performed on $10^4$ flow events using a FACSScan system equipped with a LYSYS II program.

6.2. EXAMPLES

6.2.1. HIGH YIELD OF NUCLEATED RED BLOOD CELLS FROM MATERNAL BLOOD

The cell separation methods of the present invention provided a rapid procedure for the high yield enrichment of fetal cells in a cell mixture in maternal blood. Fetal nucleated red blood cells were chosen for enrichment because they represented the more abundant population of fetal cells in maternal blood that could be readily used for genetic testing by applying a number of well-established techniques. However, the number of fetal nucleated red blood cells in maternal blood were still an extremely minor population as compared to other adult nucleated cells. Thus, a rapid enrichment method was designed to minimize cell loss and maximize the number of fetal cells available for subsequent testing.

Table 1 presents results from an experiment in which "PERCOLL" was used as the density gradient material. "PERCOLL" was prepared and adjusted to physiologic osmolality of 280 mOsm/kg $H_2O$ and physiologic pH of 7.4. However, when the gradient was adjusted to different densities, the results showed that while a density of 1.0720 gr/ml or above produced at least about 50% recovery of nucleated cells from the total nucleated cell population prior to centrifugation, there was a substantial contamination of the interface with mature red blood cells when the gradient was adjusted to a density of 1.0750 gr/ml or above. Thus, in order to recover a high percentage of total nucleated cells from the starting cell mixture, but reduce mature red blood cell contamination which was undesirable for further processing of the sample, the density of 1.0720 gr/ml was chosen and further defined to an accuracy of within ±0.0002 gr/ml. These results demonstrate that there is a narrow range of densities which may be used for the high yield enrichment of nucleated cells from a blood sample.

When four cell separation methods were compared for nucleated red blood cell yield, the two methods of the present invention produced substantially higher percentages of nucleated red blood cells than the conventional method. Table 2 shows that the cell-trap tubes containing "PERCOLL" at a density of 1.0720±0.0002 gr/ml produced about a 20 fold higher number of nucleated red blood cells than the conventional method using stock "FICOLL" at a density of 1.077±0.001 gr/ml and 320 mOsm/kg $H_2O$. FIGS. 12A–12C are a visual comparison of the nucleated cells enriched by three methods. "Percoll" plus cell-trap is superior than the other two methods in cell yield. FIGS. 13A–13C show three nucleated red blood cells at different stages of differentiation isolated by the "Percoll" plus cell-trap procedure. Therefore, this result statistically increased the total number of fetal nucleated red blood cells for subsequent genetic testing. In fact, the specific procedure also enriched for fetal trophoblast cells. Furthermore, the method involving density adjusted cell sorting produced comparable results as the method requiring magnetic field depletion of $CD45^+$ undesired cell populations. However, it should be noted that if the stock "FICOLL" was adjusted to the appropriate density and osmolality, it could be used to obtain comparable cell yield as that achieved by the "PERCOLL" used herein.

TABLE 1

| Density of "PERCOLL" (gr/ml) | Percentege of Nucleated Cells Recovered from Interface After Centrifugation | Percentage of Mature Red Blood Cell Contamination |
| --- | --- | --- |
| 1.0820 | 60% | 21% |
| 1.0790 | 58% | 21% |
| 1.0770 | 56% | 25% |
| 1.0750 | 45% | 20% |
| 1.0720 | 50% | 2% |
| 1.0700 | 21% | 2.2% |
| 1.0640 | 25% | 2.1% |
| 1.0610 | 23% | 1.7% |

TABLE 2

| | Cell Number Before Separation | Percentage of Nucleated Cells Recovered from Interface | | Percentage of Nucleated Red Blood Cells | Percentage of Nucleated Fetal Red Blood Cells |
| --- | --- | --- | --- | --- | --- |
| | | After Density Centrifugation | After Anti-CD45 Depletion | | |
| Conventional Method Using "FICOLL" | $10^7$ | 14% | 0.2% | 0.01% | Undetectable |
| "FICOLL" plus Cell-trap | $10^7$ | 16% | 0.17% | 0.01% | 0.05% |
| "PERCOLL" plus Cell-trap | $10^7$ | 54% | 1.7% | 0.21% | 0.41% |
| "PERCOLL" Plus Cell-trap Plus Density Adjusted Cell Sorting | $10^7$ | 3.3% | Not Applicable | 0.23% | Not Done |

Thus, the cell-trap containing a specific density gradient material coupled with density adjusted cell sorting provide for a rapid procedure which combines two steps into a single step to process a large volume of blood samples for high yield enrichment of nucleated red blood cells. This method is also more cost-effective because it does not require the use of a magnetic field, and require fewer working hours to process multiple samples.

6.2.2. HIGH YIELD OF FETAL CELLS FOR GENETIC TESTING

The nucleated red blood cells enriched by the methods described in Section 6.2.1, supra, were subsequently examined for the presence of fetal cells. The enriched cell preparations obtained from donors who were known to be carrying a male fetus were selected for use in FISH analysis. The cells were incubated with an X-chromosome-specific probe linked to a green fluorescence dye and a Y-chromosome-specific probe linked to a red fluorescence dye. Therefore, fetal nucleated red blood cells were identified as cells with nuclei that contained a red spot and a green spot under a fluorescence microscope, while other cells were of maternal origin. The far right column of Table 2 shows that there was an eight fold increase in the number of XY (fetal) chromosomes in the cell populations prepared by one method of the invention over that by the conventional method. However, it is of interest to note that the method of using cell-trap and "FICOLL" also increased the number of fetal nucleated red blood cells to the detection threshold over the same gradient practiced without cell-trap tubes, indicating that the cell-trap was useful in increasing cell yield. It is also noteworthy that in order to obtain reliable diagnostic results involving techniques such as FISH, it is generally necessary to enrich the fetal cells to at least 0.1% of the final cell preparation in order for the enrichment method to be used as a routine procedure. In other words, a reliable diagnosis by FISH needs to examine at least 10,000 total cells in which there are at least 10 fetal cells. One method of the invention is shown herein to have clearly exceeded this limit to have enriched fetal cells to a level of 41 cells/10,000 total cells analyzed.

7. EXAMPLE: ENRICHMENT OF $CD34^+$ CELLS FROM BLOOD CELL MIXTURE

7.1. MATERIALS AND METHODS

7.1.1. PERIPHERAL BLOOD AND BONE MARROW

Apheresed peripheral blood was applied directly onto the density gradient. However, complete blood and bone marrow aspirates were processed to a buffy coat (removal of red cells) before they were applied onto the density gradient.

Patients were hydrated and treated with cyclophosphamide (4 gm/m$^2$) administered by intravenous (IV) infusion over two hours through a central venous catheter. Twenty-four hours after the completion of the cyclophosphamide infusion, patients are treated with G-CSF (Neupogen, Amgen, Thousand Oaks, Calif.) administered by subcutaneous (SC) injection at a dose of approximately 10 $\mu$g/kg/d. Apheresis was initiated upon recovery of the white blood cell count (WBC) to equal or more than $1\times10^9$/L. Apheresis was performed using a Cobe Spectra Cell Separator (Lakewood, Colo.) at a rate of 80 ml/mln for 200 min (total volume of 16 L).

7.1.2. PREPARATION OF DENSITY GRADIENTS

"PERCOLL" solution was purchased from Pharmacia Biotech (Uppsala, Sweden) and stored at 4° C. according to the recommendation of the vendor. A stock solution was prepared by mixing 12 parts of "PERCOLL" with 1 part of 10×calcium and magnesium-free phosphate buffered saline (PBS). The pH of the solution was adjusted to 7.4 and the osmolality to 280 mOsm/Kg $H_2O$. For use in separating CD34+ cells in a cell mixture, the stock solution was further diluted with calcium and magnesium-free PBS to a density of 1.0605±0.0005 gr/ml and used at room temperature. It was crucial to adjust the density of the gradient to an accuracy of within ±0.0005 gr/ml of 1.0605 gr/ml in order to ensure reproducibility and accuracy of cell separation. This was done by a high precision digital density meter such as DMA 48 (Anton PAAR U.S.A., Ashland, Va.). All procedures were performed under sterile conditions and at room temperature.

7.1.3. DENSITY GRADIENT CENTRIFUGATION OF APHERSED BLOOD AND BONE MARROW BUFFY COATS

Aphersed blood or bone marrow buffy coat samples were layered on a "PERCOLL" gradient previously adjusted to a density of 1.0605±0.0005 gr/ml, an osmolality of 280 mOsm/Kg $H_2O$, and a pH of 7.4 in a 50 ml conical cell-trap tube or a commercially available tube. The cell-trap tube contained a constriction in a location so that approximately 15 ml of "PERCOLL" was in the lower compartment and 5 ml of "PERCOLL" was above the constriction. It was critical to completely fill the volume under the constriction with "PERCOLL" to prevent the formation of air bubbles. Generally, 20 ml of apheresed blood samples were layered on top of this gradient. The tube was centrifuged at 850×g for 30 minutes at room temperature. The cells lodged at the interface of the gradient; i.e., on top of "PERCOLL," were collected by pouring the entire content of the upper compartment of the tube into another 50 ml tube. The cell pellet in the region below the constriction were prevented from pouring off when the tube was inverted.

In order to compare the cell separation method described in the preceding paragraph with conventional methods, the test samples were also was layered on "FICOLL-HYPAQUE" (Pharmacia). The density of the stock "FICOLL" solution was at 1.077±0.001 gr/ml and the osmolality at 320 mOsm/kg $H_2O$ as published by the vendor.

7.1.4. DENSITY ADJUSTED CELL SORTING

Apheresed blood product was incubated with 1.4μ aminopropyl glass beads (Bangs Laboratories Inc., Carmel, Ind.) that were glutaraldehyde coated with an anti-CD45 antibody (clone ALB-12, Biodesign International, Kennebunk, Me.) for 45 minutes at room temperature. The entire blood cell mixture was layered on "PERCOLL" (1.0605±0.0005 gr/ml, 280 mOsm/Kg $H_2O$, pH 7.4) in a 50 ml tube.

7.1.5. MONOCLONAL ANTIBODIES

Phycoerythrin-conjugated (PE) anti-CD34 monoclonal antibodies (hematopoietic progenitor cell marker) and fluorescein-conjugated (FITC) anti-CD45 monoclonal antibodies (pan-leukocyte marker) were obtained from Becton Dickinson, Inc. (San Jose, Calif.). Unconjugated antibodies directed to CD45, CD16 (granulocytes, monocytes), CD3 (T cells), CD14 (monocytes) were prepared in the laboratory, according to methods well known in the art.

7.1.6. CONJUGATION OF MONOCLONAL ANTIBODIES TO CARRIER PARTICLES

Antibodies were conjugated to either goat anti-mouse coated magnetic beads or to goat anti-mouse coated aminopropyl glass beads by overnight incubation at room temperature. Alternatively, the antibodies could be bound directly to these beads without the goat anti-mouse bridge or could be bound via an avidin-biotin coupling reaction. In addition the antibodies could be cleaved into Fab2 fragments in order to reduce non-specific binding of cells to the beads via their Fc portion.

7.1.7. ANTIBODY STAINING AND FLOW CYTOMETRIC ANALYSIS

The cells were incubated with 10 μL of an antibody and the DNA dye LDS 751 (Exciton Inc., Dayton Ohio) per $10^6$ cells for 30 min. on ice in the presence of 5% rabbit serum. Rabbit serum was used to reduce non-specific binding to the cells. The cells were washed twice with PBS and subsequently fixed with 1% paraformaldehyde. Statistical analysis was performed on $10^4$ flow events using a FACSScan flow cytometry system equipped with a LYSYS II program.

7.1.8. COLONY FORMING (CFU) ASSAY/ FUNCTIONAL DETERMINATION OF COMMITTED CD34+ CELLS

The functional characteristics of the CD34+ cells in a cell sample was determined by the colony formation assay (CFU). This assay allowed the quantification of the number of committed hematopoietic progenitor cells in the cell solution. $10^5$ cells were mixed in 2 mL semi-solid methyl cellulose containing different colony stimulating factors and erythropoietin (Terry Fox Laboratories, Vancouver). The entire mixture was incubated for 14 days at 37° C. The number of erythroid (CFU-E, BFU-E), granulocyte/macrophage (CFU-GM) and mixed (CFU-GEMM) colonies were counted under an inverted microscope (40×).

7.1.9. LONG TERM CULTURE INITIATING CELL (LTC-IC) ASSAY/FUNCTIONAL DETERMINATION OF UNCOMMITTED CD34+ CELLS

The number of uncommitted hematopoietic progenitor cells in a cell mixture was determined by the long term culture initiating culture. The cells were seeded on an irradiated stroma feeder layer and a determination of CFU's was made in function of time. Hematopoietic stem cells were able to self-renew and gave rise to CFU's in this system for a period that exceeded 5 weeks. Long term bone marrow stromal cultures were initiated in 96 well plates ($10^6$ cells in 200 μl per well) in α-MEM medium supplemented with 12.5% horse serum, 12.5% fetal calf serum, 2 mM L-glutamine, 0.2 mM i-inositol, 20 μM folic acid, $10^{-4}$M 2-mercaptoethanol and were kept at 33° C. in a humidified atmosphere. At weekly intervals, half the medium was removed and replaced by an equal volume of fresh medium. After 2 weeks of culture, the confluent stroma layers were gamma irradiated (2000 rad) to kill endogenous hematopoietic cells. Unfractionated samples and cell preparations after separation were seeded onto the irradiated stroma layers in the same medium supplemented with $10^{-6}$M hydrocortisone. After five weeks of culture the adherent and non-adherent cells were collected and screened in the CFU assay as in Section 6.1.8, infra.

7.1.10. NATURAL KILLER (NK) CELL ASSAY

K562 target cells were labeled with 100 μCi $^{51}$Cr for 1 hour at 37° C. and then washed four times and counted. The target cells were co-cultured for 4 hours in V-bottom 96 well multiwell plates with unfractionated apheresed blood and cells from the different fractions after cell separation. Effector and target cells were mixed at different ratios, 100:1, 50:1, 25:1 and 12:1. For example, the 100:1 ratio contained $5 \times 10^5$ effector cells and $5 \times 10^3$ target cells. After the incubation period, 100 μl of the supernatant was harvested and counted in a scintillation counter. Maximal and spontaneous $^{51}$Cr release was measured counting either 50 μl of the stock target solution and supernatant from the effectors by themselves, respectively. The percent cytotoxicity was determined according to formula:

$$\text{Percent Cytotoxicity} = \frac{cpm \text{ experiment} - cpm \text{ spontaneous release}}{cpm \text{ maximal release} - cpm \text{ spontaneous release}}$$

7.1.11. MIXED LYMPHOCYTE CULTURE AND NATURAL SUPPRESSOR CELL ACTIVITY

Cells from two different buffy coats were mixed in a flat bottom 96 well multiwell plate at $10^5$ cells of each. One of the buffy coats received 3000 rad and was referred to as the "stimulators". The other buffy coat was used untreated and referred to as "responders." Unfractionated apheresed peripheral blood products (APBL) or cells from the different density fractions were added to these co-cultures at $10^5$ cells per well. These cells were referred to as "suppressors" and received 1500 rad prior to being added to the MLR. The cells were cultured for 5 days and then pulsed with [$^3$H]-thymidine (1 μCi/well). 18 hours later, the cells were harvested and the amount of thymidine incorporated determined in a scintillation counter. The percent suppression induced by the suppressor cells was determined by the formula: the amount of thymidine incorporated determined in a scintillation counter. The percent suppression induced by the suppressor cells was determined by the formula:

$$\text{Percent Suppression} = \frac{cpm \text{ control} - cpm \text{ experiment}}{cpm \text{ experiment}}$$

7.2. EXAMPLES

7.2.1. ENRICHMENT OF HEMATOPOIETIC STEM CELLS FROM BLOOD

Table 3 presents results from an experiment in which "PERCOLL" was used as the density gradient material. "PERCOLL" was prepared and adjusted to physiologic osmolality of 280±10 mOsm/kg $H_2O$ and physiologic pH of 7.4. For this study, the starting cell mixture was a sample of apheresed blood from a non-Hodgkin lymphoma patient who had been treated with G-CSF. When the gradient was adjusted to different densities, the results showed that when the density was at 1.0600 gr/ml or above, there was an about 60–90% increase of CD34$^+$ cells in the interface fraction over the gradients adjusted to lower densities. Furthermore, the percentage of total cell yield also increased slightly at 1.0600 gr/ml or above. Thus, in order to recover a high percentage of total CD34$^+$ cells from the starting cell mixture, the density of 1.0605 gr/ml was chosen. It was further determined that an accuracy of within ±0.0005 gr/ml was preferable to ensure high yield enrichment of CD34$^+$ cells.

TABLE 3

| Density "PERCOLL" (gr/ml) | | Percentage of Total Cell Yield | Percentage of CD34$^+$ Cell Yield |
|---|---|---|---|
| Unfractionated | | 100% | 100% |
| 1.0590 | Interface | 11% | 32% |
| | Pellet | 85% | 68% |
| 1.0595 | I | 18% | 45% |
| | P | 78% | 55% |
| 1.0600 | I | 26% | 80% |
| | P | 70% | 20% |
| 1.0605 | I | 31% | 83% |
| | P | 63% | 17% |
| 1.0610 | I | 35% | 89% |
| | P | 60% | 11% |

Additionally, "PERCOLL" was adjusted to a density of 1.0605 gr/ml and osmolality of 280 mOsm/kg $H_2O$, and compared with stock "FICOLL" which had a density of 1.077±0.001 gr/ml and 320 mOsm/kg $H_2O$. Table 4 shows that when the gravitational force of centrifugation increased, more CD34$^+$ cells were pelleted in the stock "FICOLL" gradient. Since the use of unadjusted "FICOLL" was the standard material used for density gradient separation of CD34$^+$ cells from a cell mixture, these results show that a precisely defined density range could substantially enhance the high yield enrichment of CD34$^+$ cells from a cell mixture. As shown in Table 4, the percentage of CD34$^+$ cell yield after centrifugation at 1500×g increased about 2 fold over that achieved by a conventional method.

TABLE 4

| | "FICOLL" | | "PERCOLL" | |
|---|---|---|---|---|
| Gravitational Force (xg) | Percentage of CD34$^+$ Cell Purity | Percentage of CD34$^+$ Cell Yield | Percentage of CD34$^+$ Cell Purity | Percentage of CD34$^+$ Cell Yield |
| 200 | 0.62% | 1% (Baseline) | 0.83% | 0.64% |
| 350 | 0.63% | 1.07% | 0.85% | 0.49% |
| 800 | 0.74% | 0.6% | 1.92% | 0.88% |
| 1500 | 0.62% | 0.48% | 2.05% | 0.83% |

Absolute cell numbers and cell recovery were determined using apheresed blood samples from non-Hodgkin lymphoma patients. The mean cell recovery from 5 samples was variable but was always in the range of 90%. Since cell counting was performed after a washing step, that may account for cell loss up to 10%. CD34$^+$ cell recovery was determined from the 5 different blood samples, and was always in the range of 90%. This result was similar to the non-specific cell loss shown above, thus it was not due to a specific depletion of the total number of CD34$^+$ cells or a change in the CD34 expression by hematopoietic progenitor cells. When the quantitative recovery of CFU's was determined, the recovery of CFU was also in the range of 90%. Therefore, the cell separation procedure by the 1.0605 gr/ml density gradient did not change the functional potential of hematopoietic progenitor cells to form colonies.

In addition, the quantitative distribution of the CFU over the gradient was determined. The results in FIG. 14 show that only minor numbers of CFU were observed in the pellet fractions and approximately 90–100% of the CFU were present in the interface of 1.0605 gr/ml "PERCOLL". This result directly correlated with the quantitative distribution of CD34$^+$ cells on the gradient as shown in Table 3. Also, it was observed that 100% of the CFU-GEMM were present in the interface (FIG. 15). LTC-IC assays showed that between 90–100% of the uncommitted hematopoietic stem cells were present in the interface (FIG. 16).

Hence, these data demonstrate that the centrifugation of apheresed blood on a single-layer gradient adjusted to 1.0605±0.0005 gr/ml resulted in a minor non-specific loss (10% or less) of the total cell product. However, while the interface represented approximately 30% of the total cell number, this cell population contained 70–90% of the CD34+ cells and more than 90% of the CFU's. The interface contained 100% of the CFU-GEMM, and since CFU-GEMM represented progenitor cells with a low degree of hematopoietic commitment and a limited degree of self renewal, the interface also contained the uncommitted hematopoietic stem cells. The results obtained with the LTC-IC assays further support this conclusion. This simplified procedure may allow the automation of CD34+ cell enrichment in a completely closed system. Furthermore, experiments performed in cell-trap tubes produced similar results with an even greater degree of consistency.

7.2.2. ADDITIONAL BIOLOGICAL FEATURES OF DENSITY SEPARATED BM AND APBL PRODUCTS

Graft versus host disease (GvHD) is induced by the T-cells that are present in the donor allografts. Consequently, some transplant protocols included the total removal of T-cells from the graft prior to transplantation. Although these methods successfully reduced GvHD, they also resulted in increased incidence of graft failure and tumor relapse. In other words, the presence of a limited number of T-cells may be beneficial for the survival chances of allotransplant patients. In this context, a "PERCOLL" gradient was adjusted to a density of 1.0605±0.0005 gr/ml to test for its ability to remove T-cells. Normal bone marrow and apheresed blood samples from G-CSF treated normal individuals were processed on the density gradient. The cells from the interface and pellet fractions were stained with the T-cell specific anti-CD3 antibodies. FIG. 17 shows that for both tissue sources the interface contained between 10% and 20% of the total number of T-cells that were present in the unprocessed material.

In vitro studies showed that human bone marrow contained low density cells which blocked in vitro alloresponses in the mixed lymphocyte reactions (MLR). Based on the fact that this suppressive activity was HLA non-restricted, it was referred to in the literature as natural suppressor (NS) activity. A "PERCOLL" density gradient was adjusted to a density of 1.0605±0.0005 gr/ml to test for its ability to enrich cells with NS activity. Apheresed blood samples from lymphoma patients and from normal individuals that received G-CSF treatment were centrifuged on a discontinuous five layer gradient, and the interfaces and pellet were screened for their potential to suppress the mixed lymphocyte culture. FIG. 18 shows that cells with NS activity had a density equal or lighter than 1.0605 gr/ml. Consequently, more than 90% of the NS activity was present in the final cell preparation after centrifugation on a 1.0605 gr/ml gradient.

NK cells had been shown to kill autologous tumor cells. From a clinical perspective, it may be beneficial to have increased numbers of NK cells in the transplant to reduce tumor relapse. In this context, the density of the NK cells was determined on a discontinuous five-layer "PERCOLL" gradient. NK cells also showed a density equal to or lighter than 1.0605 gr/ml. Consequently, more than 90% of NK cells was present in the final cell preparation after centrifugation on a 1.0605 gr/ml gradient, as shown in FIG. 19.

7.2.3. ENRICHMENT OF CD34+ CELLS USING DENSITY ADJUSTED CELL SORTING

FIGS. 20A–20F show the result of a representative experiment in which CD34+ cells were enriched by removing CD34− cells with an anti-CD45 mAb coupled to a heavy carrier (such as magnetic beads or aminopropyl glass beads). In this particular experiment the total cell number was reduced 82% and the CD34 yield was around 40%. The CD34 purity increased from 2% to approximately 20%. Since the anti-CD45 antibody removed also some of the CD34+ cells, this method could improved by using a mixture of other antibodies to deplete non-stem cells.

8. EXAMPLE: DETERMINATION OF DENSITY OF BREAST TUMOR CELL DENSITY AND THEIR ENRICHMENT BY DENSITY GRADIENT CENTRIFUGATION

8.1 MATERIALS AND METHODS

Cells were incubated with $^3$H thymidene for 24 hours under standard culture conditions according to methods known in the art. The cells were mixed with buffy coat from peripheral blood.

8.1.1. PREPARATION OF DENSITY GRADIENTS

"PERCOLL" solution was purchased from Pharmacia Biotech (Upsala, Sweden) and stored at 4° C. according to the recommendation of the vendor. A stock solution was prepared by mixing 12 parts of "PERCOLL" with 1 part of 10×calcium and magnesium-free phosphate buffered saline (PBS). The pH of the solution was adjusted to 7.4 and the osmolality to 280 mOsm/Kg H$_2$O. For use in enriching breast tumor cells obtained from in vitro cell lines in a cell mixture, the stock solution was further diluted with calcium and magnesium-free PBS into five different fractions with respective densities of 1.0490, 1.0520, 1.0550, 1.0580, and 1.0610 and used at room temperature. It was crucial to adjust the density of the gradient with an accuracy of ±0.0002 gr/ml point in order to ensure reproducibility and accuracy of cell separation. This was done by a high precision digital density meter such as DMA 48 (Anton PAAR U.S.A., Ashland, Va.). All procedures were performed under sterile conditions and at room temperature.

8.1.2. DENSITY GRADIENT CENTRIFUGATION

Radioactively labeled breast cancer cells were mixed with a buffy coat from a healthy donor and centrifuged on the discontinuous gradient. Cell mixtures containing the breast tumor cells from cell lines 30 HTB, 126 HTB, 1500 CRL and 1504 CRL were layered on a "PERCOLL" gradients previously adjusted to a densities in the range of 1.0490–1.0610, ±0.0002 gr/ml, an osmolality of 280 mOsm/Kg H$_2$O, and a pH of 7.4 in a 50 ml conical cell-trap tube. The tube contained a constriction in a location so that approximately 15 ml of "PERCOLL" was in the lower compartment and 50 ml of "PERCOLL" was above the constriction. It was critical to completely fill the volume under the constriction with "PERCOLL" to prevent the formation of air bubbles. Generally, 20 ml of cell samples were layered on top of this gradient. The tube was centrifuged at 850×g for 30 minutes at room temperature. The cells lodged at the interface of the gradient; i.e., on top of "PERCOLL," were collected by pouring the entire content of the upper compartment of the tube into another 50 ml tube. The cell pellet in the compartment below the constriction were prevented from pouring off when the tube was inverted. After centrifugation at 650×g for 10 minutes at room temperature, the fluid on top of the pellet was removed with a pipette, and the cells in the pellet resuspended in PBS. Since this low speed centrifugation step was primarily used to concentrate the cells of interest into a pellet, while removing cell debris and platelets in the fluid, a cell-trap could also be used to facilitate this step. In this alternative embodiment, a modified 50 ml cell-trap tube was used in which the constriction was placed near the bottom of the tube so that a small volume of about 0.5 ml was below it. This design protects the pellet and reduces call loss during removal of the fluid above the pellet after centrifugation. This specific feature would allow the method of the invention to be automated without the need for cell sorting. Which was performed to reduce contaminating cells, particularly platelets.

8.2 RESULTS

The densities of four breast tumor lines were determined using "PERCOLL" discontinuous density gradient system (FIGS. 21A–22D). The cells were collected from each of the interfaces and counted in a hemocytometer. The results showed that 30 to 60% of the tumor cells have a density equal to or higher than 1.0580 g/ml (FIGS. 22A–22D). This implies that the fraction containing tumor cells was between 10 and 80% pure. Of the cells collected in a specific density of 1.0580, approximately 75 to 85% of the total cells were tumor cells, while approximately 10% of the total cell volume was a contaminant. This implies that the detection limit of the assay is improved approximately 10 times from $1/10^6$ to $1/10^5$.

When radioactively labeled breast tumor cells were mixed with a peripheral blood buffy coat, up to 80% of them could be removed by centrifuging the mixture on a 1.0580 g/ml, 280 mOsm gradient. In addition, only a small fraction (<10% of initial cell number) of non-tumor cells contaminated the collected tumor fraction.

Applicants believe that the density ranges shown in FIGS. 21A–21D and 22A–22D, obtained from using cultured breast tumor cells, are applicable to breast tumor cells obtained from in vivo sources. It will be apparent to those of skill in the art that slight variations in the densities of various breast tumor cells from in vivo sources may necessitate refinement of the exact density necessary to achieve optimum enrichment. Methods for determining specific densities with an accuracy of ±0.0002 gr/ml are disclosed herein.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

9. EXAMPLE: METHOD FOR BINDING ANTIBODY TO GLASS BEADS

9.1 PREPARATION OF THE BEADS

Silica beads (1.4 micron) obtained from Bangs Laboratories, Carmel, Ind. were washed with concentrated HCl for 2 hours at room temperature and vortexed intensely every 15 minutes to brake up bead clumps. After washing, the beads were centrifuged at 850 g for 5 minutes. The HCL containing supernatant was decanted and the beads were washed with deionized $H_2O$ with intensive vortexing to brake up the clumps. The beads were incubated at room temperature overnight in concentrated nitric acid with constant stirring using a magnetic stirrer. The beads were then centrifuged at 850 g for 5 minutes and washed 3 times with deionized water, using 50 ml of deionized $H_2O$ at each step. The beads were vortexed intensely in between each wash to avoid bead clumping. To prevent microbacterial contamination, the beads were stored at 0–4 degrees centigrade in deionized $H_2O$ until further use.

9.2 SILANIZATION OF THE BEADS

To silanize the beads, either 3-aminopropyltriethoxysilane, (3-iodopropyl) trimethoxysilane or [1-9trimethoxysilyl)-2(m-(or p) chloromethyl)phenyl]ethane were used. Forty mls of silane solution (a 10% solution in 95% ethanol/deionized $H_2O$) was added per 4 gr of beads. The bead mixture was rotated end over end for 1 hour at room temperature. The beads were centrifuged at 850 g for 5 minutes and the excess silane was washed off using 95% ethanol/deionized H.0 in a volume of 100 ml. The beads were vortexed intensely in between each wash step to avoid bead clumping. After the washing step, the beads can be dried and stored. Alternatively the beads can be stored in 95% ethanol/deionized $H_2O$ in the cold which prevents clumping of the beads.

9.3 ANTIBODY COUPLING TO THE AMINOPROPYL GLASS

The silanized, beads were incubated overnight in 2.5% glutaraldehyde at room temperature. The next day, the beads were centrifuged at 850 g for 5 minutes and the free glutaraldehyde was washed off with deionized $H_2O$ in a volume of 100 ml per 5 gr beads. The beads were vortexed intensely in between each wash step to avoid bead clumping.

The antibody was added to the aminopropyl beads in an excess, at least 3 $Mg/M^2$ total bead surface and rotated end over end overnight at room temperature. The next day, the beads were centrifuged at 850 g for 5 minutes and the free protein was washed off with 100 ml of deionized $H_2O$. The beads were vortexed intensely in between each wash step to avoid bead clumping. The beads were stored in deionized $H_2O$ containing 0.1 sodium azide in the cold. The final bead suspension should contain 70–90% of single beads and the remaining 10–30% beads should be predominantly duplets and triplets.

The binding efficiency of the antibody conjugated beads (in terms of the percent of beads that are coated) can be determined using flow cytometric analysis and a fluoresceinated antibody directed to the coupled antibody. Alternatively, the antibody may be added to the silanized beads directly without the glutaraldehyde linking.

Various modifications of the invention, in addition to those shown and described herein, will become apparent to those skilled in the art from the foregoing description. Such modifications are intended to fall within the scope of the appended claims.

All references cited herein are hereby incorporated by reference in their entirety.

What is claimed is:

1. A centrifugation tube which, prior to centrifugation of said tube, comprises:

a tube adapted for centrifugation having a first closed end defining an inner bottom wall and an opposite open end;

an annular member disposed in said tube and defining an opening therethrough, wherein said opening has an area less than the area of a cross section of said tube, said annular member defining a lower portion of the tube extending between said member and the tube bottom wall and an upper portion above said annular member; and a density gradient solution filling said lower portion and a part of said upper portion to a level above said annular member.

2. The tube of claim 1, wherein said density gradient solution fills the upper portion to a level at least about 1 mm above said annular member.

3. The tube of claim 1, wherein said annular member is formed integrally with said tube.

4. The tube of claim 1, wherein said annular member is slideably disposed within said tube to permit adjustment of the volume of the lower portion.

5. The tube of claim 1 wherein said annular member defines a plurality of openings.

6. The tube of claim 1 wherein said density gradient solution has an osmolality of 280±10 mOsm kg/$H_2O$ and a specific density selected from the range 1.0300 gr/ml to 1.2000 gr/ml.

7. A method of enriching for a population of desired cells from a cell mixture containing multiple cell populations, comprising:

layering a cell mixture containing the desired cells onto a gradient density solution contained in a centrifuge tube;

said tube having a first closed end defining an inner bottom wall and an opposite open end; an annular member disposed in said tube and defining an opening therethrough, wherein said opening has an area less than the area of a cross section of said tube, said annular member defining a lower portion of the tube extending between said member and said tube bottom wall and upper portion above said annular member; said tube containing a density gradient solution which fills said lower portion and a part of said top portion to a level above said annular member;

said density gradient solution having an osmolality of 280±10 mOsm/kg $H_2O$ and a specific density within 0.0005 gr/ml of the specific density of the desired cell;

centrifuging said tube at a gravitational force sufficient to pellet cells having specific densities greater than the specific density of the density gradient material in said tube; and collecting from upper portion of said tube an enriched fraction of said population of cells.

8. The method of claim 7 wherein the specific density is within 0.0002 gr/ml of the specific density of said desired cells.

9. The method of claim 7 further comprising incubating said cell mixture with a cell type-specific binding agent linked to carrier particles prior to centrifugation, said particles having a specific density that is at least 0.001 gr/ml greater than the specific density of the desired cells.

10. The method of claim 9 wherein the cell type-specific binding agent is an antibody.

11. The method of claim 9 wherein the cell type-specific binding agent is a lectin.

12. The method of claim 9 wherein the cell type-specific binding agent is a cytokine.

13. The method of claim 9 wherein the carrier particle is a silica bead.

* * * * *